(12) United States Patent
Mathvink et al.

(10) Patent No.: US 7,208,498 B2
(45) Date of Patent: Apr. 24, 2007

(54) PIPERIDINO PYRIMIDINE DIPEPTIDYL PEPTIDASE INHIBITORS FOR THE TREATMENT OF DIABETES

(75) Inventors: Robert J. Mathvink, Red Bank, NJ (US); Scott D. Edmondson, New York, NY (US); Ann E. Weber, Scotch Plains, NJ (US)

(73) Assignee: Merck & Co., Inc., Rahway, NJ (US)

( * ) Notice: Subject to any disclaimer, the term of this patent is extended or adjusted under 35 U.S.C. 154(b) by 240 days.

(21) Appl. No.: 10/520,839

(22) PCT Filed: Jul. 11, 2003

(86) PCT No.: PCT/US03/21758

§ 371 (c)(1),
(2), (4) Date: Jan. 7, 2005

(87) PCT Pub. No.: WO2004/007468

PCT Pub. Date: Jan. 22, 2004

(65) Prior Publication Data

US 2006/0040963 A1 Feb. 23, 2006

Related U.S. Application Data

(60) Provisional application No. 60/395,846, filed on Jul. 15, 2002.

(51) Int. Cl.
*C07D 239/72* (2006.01)
*A61K 31/519* (2006.01)
*A61P 3/10* (2006.01)
*A61P 3/06* (2006.01)
*A61P 3/04* (2006.01)
*A61P 5/28* (2006.01)
*A61P 35/00* (2006.01)

(52) U.S. Cl. .................... 514/258.1; 544/279
(58) Field of Classification Search ............... 544/279; 514/258.1
See application file for complete search history.

(56) References Cited

U.S. PATENT DOCUMENTS

| 4,386,090 A | 5/1983 | Moinet et al. |
| 5,939,560 A | 8/1999 | Jenkins et al. |
| 6,011,155 A | 1/2000 | Villhauer |
| 6,166,063 A | 12/2000 | Villhauer |
| 6,303,661 B1 | 10/2001 | Demuth et al. |
| 6,432,969 B1 | 8/2002 | Villhauer |
| 6,699,871 B2 | 3/2004 | Edmondson et al. |

FOREIGN PATENT DOCUMENTS

| WO | WO 97/40832 | 11/1997 |
| WO | WO 98/19998 A2 | 5/1998 |
| WO | WO 98/19998 A3 | 5/1998 |
| WO | WO 00/34241 | 6/2000 |
| WO | WO 01/34594 A1 | 5/2001 |
| WO | WO 01/42262 | 6/2001 |
| WO | WO 01/96295 A2 | 12/2001 |
| WO | WO 01/96295 A3 | 12/2001 |
| WO | WO 02/02560 A2 | 1/2002 |
| WO | WO 02/02560 A3 | 1/2002 |
| WO | WO 02/076450 A1 | 10/2002 |
| WO | WO 03/000180 A2 | 1/2003 |
| WO | WO 03/000180 A3 | 1/2003 |
| WO | WO 03/000181 A2 | 1/2003 |
| WO | WO 03/000181 A3 | 1/2003 |
| WO | WO 03/082817 A2 | 10/2003 |
| WO | WO 2004/007468 | 1/2004 |
| WO | WO 2004/007468 A1 | 1/2004 |
| WO | WO 2004/032836 A2 | 4/2004 |
| WO | WO 2004/043940 | 5/2004 |
| WO | WO 2004/050022 A2 | 6/2004 |
| WO | WO 2004/058266 A1 | 7/2004 |
| WO | WO 2004/064778 A2 | 8/2004 |
| WO | WO 2004/069162 A2 | 8/2004 |
| WO | WO 2004/110436 | 12/2004 |
| WO | WO 2004/112701 A2 | 12/2004 |
| WO | WO 2004/112701 A3 | 12/2004 |
| WO | WO 2005/011581 A2 | 2/2005 |

OTHER PUBLICATIONS

Green et al., Expert Opin. Emerging Drugs, 11(3); 525-539, 2006.*
J. J. Holst, "Treatment of Type 2 Diabetes Mellitus with Agonists of the GLP-1 Receptor or DPP-IV Inhibitors", Expert Opin. Emerg. Drugs, vol. 9(1) pp. 155-166, 2004.
C. F. Deacon, et al., "Inhibitors of dipeptidyl peptidase IV: A Novel Approach for the Prevention and Treatment of Type 2 Diabetes?", Expert Opin. Investig. Drugs, vol. 13(9) pp. 1091-1102, 2004.
K. Augustyns et al., "Dipeptidyl Peptidase IV Inhibitors as New Therapeutic Agents for the Treatment of Type 2 Diabetes", Expert Opin. Ther. Patents, vol. 13(4), pp. 499-510, 2003.
Novartis AG: WO0034241, "Novel N-substituted-2-Cyanopyrrolidines as Potent Inhibitors of Dipeptidyl Peptidase IV in the Treatment of Non-Insulin-Dependent Diabetes Mellitus", Exp. Opin. Ther. Patents, vol. 10(12), pp. 1937-1942, 2000.
O. J. Orucker, "Therapeutic potential of dipeptidyl peptidase IV inhibitors for the treatment of type 2 diabetes", Exp. Opin Invest. Drugs, vol. 12, 2004, pp. 87-100.
T. P. Vahl & D. A. D'Alessio, "Gut peptides in the treatment of diabetes mellitus" Exp. Opin. Invest. Drugs, vol. 13, 2004, pp. 177-188.

(Continued)

*Primary Examiner*—Venkataraman Balasubramanian
(74) *Attorney, Agent, or Firm*—Philippe L. Durette; Melvin Winokur

(57) ABSTRACT

The present invention is directed to compounds which are inhibitors of the dipeptidyl peptidase-IV enzyme ("DP-IV inhibitors") and which are useful in the treatment or prevention of diseases in which the dipeptidyl peptidase-IV enzyme is involved, such as diabetes and particularly Type 2 diabetes. The invention is also directed to pharmaceutical compositions comprising these compounds and the use of these compounds and compositions in the prevention or treatment of such diseases in which the dipeptidyl peptidase-IV enzyme is involved.

21 Claims, No Drawings

OTHER PUBLICATIONS

L. B. Knudsen, "Glucagon-like peptide-1: The Basis of a New Class of Treatment for Type 2 Diabetes", J. Med. Chem, vol. 47, 2004, pp. 4128-4134.

Ann E. Weber, "Dipeptidyl Peptidase IV Inhibitors for the Treatment of Diabetes", J. Med. Chem, vol. 47, 2004, pp. 4135-4141.

J. J. Holst and C. F. Deacon, "Glucagon-like peptide 1 and inhibitors of dipeptidyl peptidase IV in the treatment of type 2 diabetes mellitus", Curr. Opin Pharmacology, vol. 4, 2004, pp. 589-596.

C. F. Deacon, "Perspectives in Diabetes—Therapeutic Strategies Based on Glucagon-Like Peptide 1", Diabetes, vol. 53, Sep. 2004, pp. 2181-2189.

* cited by examiner

PIPERIDINO PYRIMIDINE DIPEPTIDYL PEPTIDASE INHIBITORS FOR THE TREATMENT OF DIABETES

CROSS REFERENCE TO RELATED APPLICATIONS

This application is the National Stage of International Application No. PCT/US03/21758 filed 11 Jul. 2003, which claims the benefit under 35 U.S.C. 119(e) of U.S. Provisional Application No. 60/395,846, filed 15 Jul. 2002.

BACKGROUND OF THE INVENTION

Diabetes refers to a disease process derived from multiple causative factors and characterized by elevated levels of plasma glucose or hyperglycemia in the fasting state or after administration of glucose during an oral glucose tolerance test. Persistent or uncontrolled hyperglycemia is associated with increased and premature morbidity and mortality. Often abnormal glucose homeostasis is associated both directly and indirectly with alterations of the lipid, lipoprotein and apolipoprotein metabolism and other metabolic and hemodynamic disease. Therefore patients with Type 2 diabetes mellitus are at especially increased risk of macrovascular and microvascular complications, including coronary heart disease, stroke, peripheral vascular disease, hypertension, nephropathy, neuropathy, and retinopathy. Therefore, therapeutical control of glucose homeostasis, lipid metabolism and hypertension are critically important in the clinical management and treatment of diabetes mellitus.

There are two generally recognized forms of diabetes. In type 1 diabetes, or insulin-dependent diabetes mellitus (IDDM), patients produce little or no insulin, the hormone which regulates glucose utilization. In Type 2 diabetes, or noninsulin dependent diabetes mellitus (NIDDM), patients often have plasma insulin levels that are the same or even elevated compared to nondiabetic subjects; however, these patients have developed a resistance to the insulin stimulating effect on glucose and lipid metabolism in the main insulin-sensitive tissues, which are muscle, liver and adipose tissues, and the plasma insulin levels, while elevated, are insufficient to overcome the pronounced insulin resistance.

Insulin resistance is not primarily due to a diminished number of insulin receptors but to a post-insulin receptor binding defect that is not yet understood. This resistance to insulin responsiveness results in insufficient insulin activation of glucose uptake, oxidation and storage in muscle and inadequate insulin repression of lipolysis in adipose tissue and of glucose production and secretion in the liver.

The available treatments for Type 2 diabetes, which have not changed substantially in many years, have recognized limitations. While physical exercise and reductions in dietary intake of calories will dramatically improve the diabetic condition, compliance with this treatment is very poor because of well-entrenched sedentary lifestyles and excess food consumption, especially of foods containing high amounts of saturated fat. Increasing the plasma level of insulin by administration of sulfonylureas (e.g. tolbutamide and glipizide) or meglitinide, which stimulate the pancreatic β-cells to secrete more insulin, and/or by injection of insulin when sulfonylureas or meglitinide become ineffective, can result in insulin concentrations high enough to stimulate the very insulin-resistant tissues. However, dangerously low levels of plasma glucose can result from administration of insulin or insulin secretagogues (sulfonylureas or meglitinide), and an increased level of insulin resistance due to the even higher plasma insulin levels can occur. The biguanides increase insulin sensitivity resulting in some correction of hyperglycemia. However, the two biguanides, phenformin and metformin, can induce lactic acidosis and nausea/diarrhea. Metformin has fewer side effects than phenformin and is often prescribed for the treatment of Type 2 diabetes.

The glitazones (i.e. 5-benzylthiazolidine-2,4-diones) are a more recently described class of compounds with potential for ameliorating many symptoms of Type 2 diabetes. These agents substantially increase insulin sensitivity in muscle, liver and adipose tissue in several animal models of Type 2 diabetes resulting in partial or complete correction of the elevated plasma levels of glucose without occurrence of hypoglycemia. The glitazones that are currently marketed are agonists of the peroxisome proliferator activated receptor (PPAR), primarily the PPAR-gamma subtype. PPAR-gamma agonism is generally believed to be responsible for the improved insulin sensititization that is observed with the glitazones. Newer PPAR agonists that are being tested for treatment of Type 2 diabetes are agonists of the alpha, gamma or delta subtype, or a combination of these, and in many cases are chemically different from the glitazones (i.e., they are not thiazolidinediones). Serious side effects (e.g. liver toxicity) have occurred with some of the glitazones, such as troglitazone.

Additional methods of treating the disease are still under investigation. New biochemical approaches that have been recently introduced or are still under development include treatment with alpha-glucosidase inhibitors (e.g. acarbose) and protein tyrosine phosphatase-1B (PTP-1B) inhibitors.

Compounds that are inhibitors of the dipeptidyl peptidase-IV ("DP-IV" or "DPP-IV") enzyme are also under investigation as drugs that may be useful in the treatment of diabetes, and particularly Type 2 diabetes. See for example WO 97/40832; WO 98/19998; U.S. Pat. No. 5,939,560; Bioorg. Med. Chem. Lett., 6(10), 1163–1166 (1996); and Bioorg. Med. Chem. Lett., 6(22), 2745–2748 (1996). The usefulness of DP-IV inhibitors in the treatment of Type 2 diabetes is based on the fact that DP-IV in vivo readily inactivates glucagon like peptide-1 (GLP-1) and gastric inhibitory peptide (GIP). GLP-1 and GIP are incretins and are produced when food is consumed. The incretins stimulate production of insulin. Inhibition of DP-IV leads to decreased inactivation of the incretins, and this in turn results in increased effectiveness of the incretins in stimulating production of insulin by the pancreas. DP-IV inhibition therefore results in an increased level of serum insulin. Advantageously, since the incretins are produced by the body only when food is consumed, DP-IV inhibition is not expected to increase the level of insulin at inappropriate times, such as between meals, which can lead to excessively low blood sugar (hypoglycemia). Inhibition of DP-IV is therefore expected to increase insulin without increasing the risk of hypoglycemia, which is a dangerous side effect associated with the use of insulin secretagogues.

DP-IV inhibitors also have other therapeutic utilities, as discussed herein. DP-IV inhibitors have not been studied extensively to date, especially for utilities other than diabetes. New compounds are needed so that improved DP-IV inhibitors can be found for the treatment of diabetes and potentially other diseases and conditions.

SUMMARY OF THE INVENTION

The present invention is directed to compounds which are inhibitors of the dipeptidyl peptidase-IV enzyme ("DP-IV inhibitors") and which are useful in the treatment or prevention of diseases in which the dipeptidyl peptidase-IV enzyme is involved, such as diabetes and particularly Type 2 diabetes. The invention is also directed to pharmaceutical compositions comprising these compounds and the use of these compounds and compositions in the prevention or treatment of such diseases in which the dipeptidyl peptidase-IV enzyme is involved.

DETAILED DESCRIPTION OF THE INVENTION

The present invention is directed to compounds of the formula I:

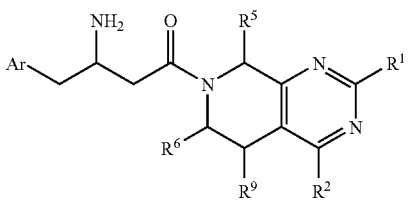

wherein:

Ar is phenyl which is unsubstituted or substituted with 1–5 of $R^3$, wherein $R^3$ is independently selected from the group consisting of:
(1) halogen,
(2) $C_{1-6}$alkyl, which is linear or branched and is unsubstituted or substituted with 1–5 halogens,
(3) $OC_{1-6}$alkyl, which is linear or branched and is unsubstituted or substituted with 1–5 halogens,
(4) CN, and
(5) OH;

$R^1$ and $R^2$ are independently selected from the group consisting of:
(1) hydrogen,
(2) CN,
(3) $C_{1-10}$alkyl, which is linear or branched and which is unsubstituted or substituted with:
  (a) halogen, or
  (b) phenyl, which is unsubstituted or substituted with 1–5 substituents independently selected from halogen, CN, OH, $R^4$, $OR^4$, $NHSO_2R^4$, $N(C_{1-6}alkyl)SO_2R^4$, $SO_2R^4$, $SO_2NR^7R^8$, $NR^7R^8$, $CONR^7R^8$, $CO_2H$, and $CO_2C_{1-6}$alkyl, wherein the $C_{1-6}$alkyl is linear or branched,
(4) phenyl which is unsubstituted or substituted with 1–5 substituents independently selected from halogen, CN, OH, $R^4$, $OR^4$, $NHSO_2R^4$, $N(C_{1-6}alkyl)SO_2R^4$, $SO_2R^4$, $SO_2NR^7R^8$, $NR^7R^8$, $CONR^7R^8$, $CO_2H$, and $CO_2C_{1-6}$alkyl, wherein the $C_{1-6}$alkyl is linear or branched,
(5) a 5- or 6-membered heterocycle which may be saturated or unsaturated comprising 1–4 heteroatoms independently selected from N, S and O, the heterocycle being unsubstituted or substituted with 1–3 substituents independently selected from oxo, halogen, $NO_2$, CN, OH, $R^4$, $OR^4$, $NHSO_2R^4$, $N(C_{1-6}alkyl)SO_2R^4$, $SO_2R^4$, $SO_2NR^7R^8$, $NR^7R^8$, $CONR^7R^8$, $CO_2H$, and $CO_2C_{1-6}$alkyl, wherein the $C_{1-6}$alkyl is linear or branched,
(6) $C_{3-6}$cycloalkyl, which is optionally substituted with 1–5 substituents independently selected from halogen, OH, $C_{1-6}$alkyl, and $OC_{1-6}$alkyl, wherein the $C_{1-6}$alkyl and $OC_{1-6}$alkyl are linear or branched and optionally substituted with 1–5 halogens,
(7) OH,
(8) $OR^4$, and
(9) $NR^7R^8$;

$R^4$ is $C_{1-6}$alkyl, which is linear or branched and which is unsubstituted or substituted with 1–5 groups independently selected from halogen, $CO_2H$, and $CO_2C_{1-6}$alkyl, wherein the $C_{1-6}$alkyl is linear or branched;

$R^5$, $R^6$ and $R^9$ are independently selected from the group consisting of:
(1) hydrogen,
(2) $C_{1-10}$alkyl, which is linear or branched and which is unsubstituted or substituted with one or more substituents selected from:
  (a) halogen,
  (b) hydroxy,
  (c) phenyl, which is unsubstituted or substituted with 1–5 substituents independently selected from halogen, OH, $C_{1-6}$alkyl, and $OC_{1-6}$alkyl, wherein the $C_{1-6}$alkyl is linear or branched and optionally substituted with 1–5 halogens,
  (d) naphthyl, wherein the naphthyl is optionally substituted with 1–5 substituents independently selected from halogen, OH, $C_{1-6}$alkyl, and $OC_{1-6}$alkyl, wherein the $C_{1-6}$alkyl is linear or branched and optionally substituted with 1–5 halogens,
  (e) $CO_2H$,
  (f) $CO_2C_{1-6}$alkyl,
  (g) $CONR^7R^8$,
(3) CN,
(4) phenyl which is unsubstituted or substituted with 1–5 substituents independently selected from $C_{1-6}$alkyl, $OC_{1-6}$alkyl, hydroxy and halogen, wherein the $C_{1-6}$alkyl is linear or branched and optionally substituted with 1–5 halogens,
(5) naphthyl which is unsubstituted or substituted with 1–5 substituents independently selected from $C_{1-6}$alkyl, $OC_{1-6}$alkyl, hydroxy and halogen, wherein the $C_{1-6}$alkyl is linear or branched and optionally substituted with 1–5 halogens,
(6) $CO_2H$,
(7) $CO_2C_{1-6}$alkyl,
(8) $CONR^7R^8$, and
(9) $C_{3-6}$cycloalkyl, which is unsubstituted or substituted with 1–5 substituents independently selected from halogen, OH, $C_{1-6}$alkyl, and $OC_{1-6}$alkyl, wherein the $C_{1-6}$alkyl is linear or branched and optionally substituted with 1–5 halogens;

$R^7$ and $R^8$ are independently selected from the group consisting of:
(1) hydrogen,
(2) phenyl, which is unsubstituted or substituted with substituents independently selected from halogen, OH, $C_{1-6}$alkyl, and $OC_{1-6}$alkyl, wherein the $C_{1-6}$alkyl is linear or branched and optionally substituted with 1–5 halogens,
(3) $C_{3-6}$cycloalkyl, which is unsubstituted or substituted with substituents independently selected from halogen, OH, $C_{1-6}$alkyl, and $OC_{1-6}$alkyl, wherein the $C_{1-6}$alkyl is linear or branched and optionally substituted with 1–5 halogens, and
(4) $C_{1-6}$alkyl, which is linear or branched and which is unsubstituted or substituted with:
  (a) halogen, or
  (b) phenyl, which is unsubstituted or substituted with 1–5 substituents independently selected from halogen, OH, $C_{1-6}$alkyl, and $OC_{1-6}$alkyl, wherein the $C_{1-6}$alkyl is linear or branched and optionally substituted with 1–5 halogens, or wherein $R^7$ and $R^8$ together with the nitrogen atom to which they are attached form a heterocyclic ring selected from azetidine, pyrrolidine, piperidine, piperazine, and morpholine wherein said heterocyclic ring is unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens;

and pharmaceutically acceptable salts thereof and individual diastereomers thereof.

An embodiment of the present invention includes compounds of the formula Ia:

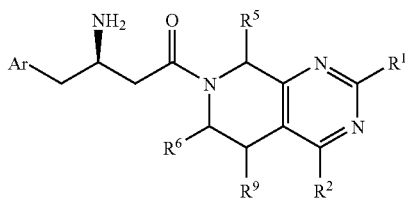

Ia wherein Ar, $R^1$, $R^2$, $R^5$, $R^6$ and $R^9$ are defined herein;

and pharmaceutically acceptable salts and individual diastereomers thereof.

Another embodiment of the present invention includes compounds of the formula Ib:

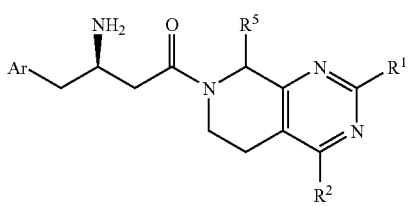

Ib wherein Ar, $R^1$, $R^2$ and $R^5$ are defined herein;

and pharmaceutically acceptable salts and individual diastereomers thereof.

Another embodiment of the present invention includes compounds of the formula Ic:

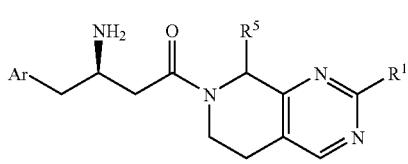

Ic wherein Ar, $R^1$ and $R^5$ are defined herein;

and pharmaceutically acceptable salts thereof and individual diastereomers thereof.

Another embodiment of the present invention includes compounds of the formula Id:

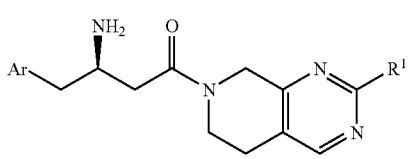

Id wherein Ar and $R^1$ are defined herein;

and pharmaceutically acceptable salts and individual diastereomers thereof.

Another embodiment of the present invention includes compounds of the formula Ie:

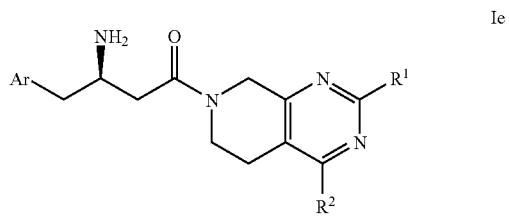

Ie wherein Ar, $R^1$ and $R^2$ are defined herein;

and pharmaceutically acceptable salts and individual diastereomers thereof.

In the present invention it is preferred that Ar is phenyl which is unsubstituted or substituted with 1–5 of $R^3$ which are independently selected from the group consisting of:
  (1) fluoro,
  (2) chloro,
  (3) bromo,
  (4) methyl,
  (5) $CF_3$, and
  (6) OH.

In the present invention it is more preferred that Ar is selected from the group consisting of:
  (1) phenyl,
  (2) 2-fluorophenyl,
  (3) 3,4-difluorophenyl,
  (4) 2,5-difluorophenyl, and
  (5) 2,4,5-trifluorophenyl.

In the present invention it is preferred that $R^1$ is selected from the group consisting of:
  (1) hydrogen,
  (2) $C_{1-6}$alkyl, which is linear or branched and which is unsubstituted or substituted with phenyl or 1–5 fluoro,
  (3) phenyl which is unsubstituted or substituted with 1–5 substituents independently selected from halogen, CN, OH, $R^4$, $OR^4$, $NHSO_2R^4$, $N(C_{1-6}alkyl)SO_2R^4$, $SO_2R^4$, $SO_2NR^7R^8$, $NR^7R^8$, $CONR^7R^8$, $CO_2H$, and $CO_2C_{1-6}$alkyl, wherein the $C_{1-6}$alkyl is linear or branched,
  (4) a 5- or 6-membered heterocycle which may be saturated or unsaturated comprising 14 heteroatoms independently selected from N, S and O, the heterocycle being unsubstituted or substituted with 1–3 substituents independently selected from oxo, halogen, $NO_2$, CN, OH, $R^4$, $OR^4$, $NHSO_2R^4$, $N(C_{1-6}alkyl)SO_2R^4$, $SO_2R^4$, $SO_2NR^7R^8$, $NR^7R^8$, $CONR^7R^8$, $CO_2H$, and $CO_2C_{1-6}$alkyl, wherein the $C_{1-6}$alkyl is linear or branched,
  (5) $C_{3-6}$cycloalkyl, and
  (6) $NR^7R^8$.

In the present invention it is more preferred that $R^1$ is selected from the group consisting of:
  (1) hydrogen,
  (2) $CF_3$,
  (3) phenyl which is unsubstituted or substituted with 1–5 substituents independently selected from halogen, methyl, $CF_3$, $OCF_3$, $NHSO_2Me$, $NHSO_2CF_3$, $SO_2Me$, $SO_2CF_3$, $SO_2NH_2$, $NH_2$, NHMe, $NMe_2$, and $CONH_2$, (4) pyridine, pyrazine, and imidazole which is unsubstituted or substituted with 1–5 substituents independently selected from $CF_3$, Me, and $NO_2$,
(5) cyclopropyl,
(6) morpholine,
(7) $NH_2$,
(8) NHMe,
(9) $NMe_2$, and
(10) $NHCH_2Ph$.

In the present invention it is more preferred that $R^1$ is selected from the group consisting of:
(1) hydrogen,
(2) $CF_3$,
(3) phenyl which is unsubstituted or substituted with 1–5 substituents independently selected from halogen, methyl, $CF_3$, $OCF_3$, $NHSO_2Me$, $SO_2Me$, $SO_2CF_3$, $SO_2NH_2$, and $CONH_2$,
(4) pyridine, pyrazine, or imidazole which is unsubstituted or substituted with 1–5 substituents independently selected from $CF_3$, Me, and $NO_2$, and
(5) cyclopropyl.

In the present invention it is even more preferred that $R^1$ is hydrogen Or $CF_3$.

In the present invention it is preferred that $R^2$ is selected from:
(1) hydrogen,
(2) $C_{1-6}$alkyl, which is linear or branched and which is unsubstituted or substituted with 1–5 fluoro,
(3) OH,
(4) $OR^4$, and
(5) $NR^7R^8$.

In the present invention it is more preferred that $R^2$ is selected from the group consisting of:
(1) hydrogen,
(2) OH,
(3) methoxy,
(4) isopropoxy,
(5) $CF_3$,
(6) $NH_2$, and
(7) NHMe.

In the present invention it is even more preferred that $R^2$ is hydrogen.

In the present invention it is preferred that $R^5$, $R^6$ and $R^9$ are independently selected from the group consisting of:
(1) hydrogen and
(2) $C_{1-10}$alkyl, which is linear or branched and which is unsubstituted or substituted with one or more substituents selected from:
  (a) halogen, and
  (b) phenyl, wherein the phenyl is optionally substituted with 1–5 substituents independently selected from halogen, OH, $C_{1-6}$alkyl, and $OC_{1-6}$alkyl, wherein the $C_{1-6}$alkyl and $OC_{1-6}$alkyl are linear or branched and optionally substituted with 1–5 halogens.

In the present invention it is more preferred that $R^5$, $R^6$ and $R^9$ are independently selected from the group consisting of:
(1) hydrogen,
(2) $CH_3$, and
(3) $CH_2$-phenyl.

In the present invention it is even more preferred that $R^5$ is H or $CH_3$ and $R^6$ and $R^9$ are hydrogen.

The compounds of the present invention may contain one or more asymmetric centers and can thus occur as racemates and racemic mixtures, single enantiomers, diastereomeric mixtures and individual diastereomers. The compounds of the instant invention have one asymmetric center at the beta carbon atom. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

Some of the compounds described herein contain olefinic double bonds, and unless specified otherwise, are meant to include both E and Z geometric isomers.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds of the present invention.

Formula I shows the structure of the class of compounds without preferred stereochemistry. Formula Ia shows the preferred stereochemistry at the carbon atom that is attached to the amino group of the beta amino acid from which these compounds are prepared.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, fumaric, and tartaric acids.

It will be understood that, as used herein, references to the compounds of Formula I are meant to also include the pharmaceutically acceptable salts.

As appreciated by those of skill in the art, halo or halogen as used herein is intended to include fluoro, chloro, bromo and iodo. Similarly, $C_{1-6}$, as in $C_{1-6}$alkyl is defined to identify the group as having 1, 2, 3, 4, 5 or 6 carbons in a linear or branched arrangement, such that $C_{1-6}$alkyl specifically includes methyl, ethyl, n-propyl, iso-propyl, n-butyl, iso-butyl, tert-butyl, pentyl, and hexyl. Likewise, $C_0$, as in $C_0$alkyl is defined to identify the presence of a direct covalent bond. A group which is designated as being independently substituted with substituents may be independently substituted with multiple numbers of such substituents. The term "heterocycle" as used herein is intended to include 5- to 10-membered ring systems which are within the following listing: benzimidazolyl, benzodioxanyl, benzofuranyl, benzopyrazolyl, benzothiadiazolyl, benzotriazolyl, benzothiophenyl, benzoxadiazolyl, benzoxazolyl, carbazolyl, carbolinyl, chromanyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolinyl, quinoxalinyl, tetrazolyl, thiadiazolyl, thiazolidinyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxyphenyl, tetrahydrofuranyl, tetrahydroimidazolyl, tetrahydroisoquinolinyl, and tetrahydrothienyl.

Exemplifying the invention is the use of the compounds disclosed in the Examples and herein.

Specific compounds within the present invention include a compound which is selected from the group consisting of the compounds disclosed in the following Examples and pharmaceutically acceptable salts thereof and individual diastereomers thereof.

The subject compounds are useful in a method of inhibiting the dipeptidyl peptidase-IV enzyme in a patient such as a mammal in need of such inhibition comprising the administration of an effective amount of the compound. The present invention is directed to the use of the compounds disclosed herein as inhibitors of dipeptidyl peptidase-IV enzyme activity.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

The present invention is further directed to a method for the manufacture of a medicament for inhibiting dipeptidyl peptidase-IV enzyme activity in humans and animals comprising combining a compound of the present invention with a pharmaceutical carrier or diluent.

The subject treated in the present methods is generally a mammal, preferably a human being, male or female, in whom inhibition of dipeptidyl peptidase-IV enzyme activity is desired. The term "therapeutically effective amount" means the amount of the subject compound that will elicit the biological or medical response of a tissue, system, animal or human that is being sought by the researcher, veterinarian, medical doctor or other clinician. As used herein, the term "treatment" refers both to the treatment and to the prevention or prophylactic therapy of the mentioned conditions.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as inhibitors of dipeptidyl peptidase-IV enzyme activity may be demonstrated by methodology known in the art. Inhibition constants are determined as follows. A continuous fluorometric assay is employed with the substrate Gly-Pro-AMC, which is cleaved by DP-IV to release the fluorescent AMC leaving group. The kinetic parameters that describe this reaction are as follows: $K_m$=50 µM; $k_{cat}$=75 s$^{-1}$; $k_{cat}/K_m$=1.5×10$^6$ M$^{-1}$s$^{-1}$. A typical reaction contains approximately 50 pM enzyme, 50 µM Gly-Pro-AMC, and buffer (100 mM HEPES, pH 7.5, 0.1 mg/ml BSA) in a total reaction volume of 100 µL. Liberation of AMC is monitored continuously in a 96-well plate fluorometer using an excitation wavelength of 360 nm and an emission wavelength of 460 nm. Under these conditions, approximately 0.8 µM AMC is produced in 30 minutes at 25 degrees C. The enzyme used in these studies was soluble (transmembrane domain and cytoplasmic extension excluded) human protein produced in a baculovirus expression system (Bac-To-Bac, Gibco BRL). The kinetic constants for hydrolysis of Gly-Pro-AMC and GLP-1 were found to be in accord with literature values for the native enzyme. To measure the dissociation constants for compounds, solutions of inhibitor in DMSO were added to reactions containing enzyme and substrate (final DMSO concentration is 1%). All experiments were conducted at room temperature using the standard reaction conditions described above. To determine the dissociation constants ($K_i$), reaction rates were fit by non-linear regression to the Michaelis-Menton equation for competitive inhibition. The errors in reproducing the dissociation constants are typically less than two-fold.

In particular, the compounds of the following examples had activity in inhibiting the dipeptidyl peptidase-IV enzyme in the aforementioned assays, generally with an $IC_{50}$ of less than about 1 μM. Such a result is indicative of the intrinsic activity of the compounds in use as inhibitors of the dipeptidyl peptidase-IV enzyme activity.

Dipeptidyl peptidase-IV enzyme (DP-IV) is a cell surface protein that has been implicated in a wide range of biological functions. It has a broad tissue distribution (intestine, kidney, liver, pancreas, placenta, thymus, spleen, epithelial cells, vascular endothelium, lymphoid and myeloid cells, serum), and distinct tissue and cell-type expression levels. DP-IV is identical to the T cell activation marker CD26, and it can cleave a number of immunoregulatory, endocrine, and neurological peptides in vitro. This has suggested a potential role for this peptidase in a variety of disease processes in humans or other species.

The compounds of the present invention have utility in treating, preventing, ameliorating, controlling or reducing the risk of one or more of the following conditions or diseases: (1) hyperglycemia, (2) low glucose tolerance, (3) insulin resistance, (4) obesity, (5) lipid disorders, (6) dyslipidemia, (7) hyperlipidemia, (8) hypertriglyceridernia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), (25) Type 2 diabetes, (26) growth hormone deficiency, (27) neutropenia, (28) neuronal disorders, (29) tumor metastasis, (30) benign prostatic hypertrophy, (32) gingivitis, (33) hypertension, (34) osteoporosis, and other conditions that may be treated or prevented by inhibition of DP-IV.

The subject compounds are further useful in a method for the prevention, treatment, control, amelioration, or reducation of risk of the diseases, disorders and conditions noted herein.

Type 2 Diabetes and Related Disorders: It is well established that the incretins GLP-1 and GIP are rapidly inactivated in vivo by DP-IV. Studies with DP-IV$^{(-/-)}$-deficient mice and preliminary clinical trials indicate that DP-IV inhibition increases the steady state concentrations of GLP-1 and GIP, resulting in improved glucose tolerance. By analogy to GLP-1 and GIP, it is likely that other glucagon family peptides involved in glucose regulation are also inactivated by DP-IV (eg. PACAP). Inactivation of these peptides by DP-IV may also play a role in glucose homeostasis. The DP-IV inhibitors of the present invention therefore have utility in the treatment, prevention, amelioration, control or reduction of the risk of Type 2 diabetes and in the treatment, prevention, amelioration, control or reduction of the risk of the numerous conditions that often accompany Type 2 diabetes, including metabolic syndrome X, reactive hypoglycemia, and diabetic dyslipidemia. Obesity, discussed below, is another condition that is often found with Type 2 diabetes that may respond to treatment with the compounds of this invention.

The following diseases, disorders and conditions are related to Type 2 diabetes, and therefore may be treated, controlled, ameliorated or prevented, by administering the compounds of this invention: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), and other disorders where insulin resistance is a component.

Obesity: DP-IV inhibitors may be useful for the treatment of obesity. This is based on the observed inhibitory effects on food intake and gastric emptying of GLP-1 and GLP-2. Exogenous administration of GLP-1 in humans significantly decreases food intake and slows gastric emptying (Am. J. Physiol. 277, R910–R916 (1999)). ICV administration of GLP-1 in rats and mice also has profound effects on food intake (Nature Medicine 2, 1254–1258 (1996)). This inhibition of feeding is not observed in GLP-1R$^{(-/-)}$ mice, indicating that these effects are mediated through brain GLP-1 receptors. By analogy to GLP-1, it is likely that GLP-2 is also regulated by DP-IV. ICV administration of GLP-2 also inhibits food intake, analogous to the effects observed with GLP-1 (Nature Medicine 6, 802–807 (2000)).

Growth Hormone Deficiency: DP-IV inhibition may be useful for the treatment of growth hormone deficiency, based on the hypothesis that growth-hormone releasing factor (GRF), a peptide that stimulates release of growth hormone from the anterior pituitary, is cleaved by the DP-IV enzyme in vivo (WO 00/56297). The following data provide evidence that GRF is an endogenous substrate: (1) GRF is efficiently cleaved in vitro to generate the inactive product GRF[3-44] (BBA 1122, 147–153 (1992)); (2) GRF is rapidly degraded in plasma to GRF [3-44]; this is prevented by the DP-IV inhibitor diprotin A; and (3) GRF[3-44] is found in the plasma of a human GRF transgenic pig (J. Clin. Invest. 83, 1533–1540 (1989)). Thus DP-IV inhibitors may be useful for the same spectrum of indications which have been considered for growth hormone secretagogues.

Intestinal Injury: The potential for using DP-IV inhibitors for the treatment of intestinal injury is suggested by the results of studies indicating that glucagon-like peptide-2 (GLP-2), a likely endogenous substrate for DP-IV, may exhibit trophic effects on the intestinal epithelium (Regulatory Peptides 90, 27–32 (2000)). Administration of GLP-2 results in increased small bowel mass in rodents and attenuates intestinal injury in rodent models of colitis and enteritis.

Immunosuppression: DP-IV inhibition may be useful for modulation of the immune response, based upon studies implicating the DP-IV enzyme in T cell activation and in chemokine processing, and efficacy of DP-IV inhibitors in in vivo models of disease. DP-IV has been shown to be identical to CD26, a cell surface marker for activated immune cells. The expression of CD26 is regulated by the differentiation and activation status of immune cells. It is generally accepted that CD26 functions as a co-stimulatory molecule in in vitro models of T cell activation. A number of chemokines contain proline in the penultimate position, presumably to protect them from degradation by non-specific aminopeptidases. Many of these have been shown to be processed in vitro by DP-IV. In several cases (RANTES, LD78-beta, MDC, eotaxin, SDF-1alpha), cleavage results in an altered activity in chemotaxis and signaling assays. Receptor selectivity also appears to be modified in some cases (RANTES). Multiple N-terminally truncated forms of a number of chemokines have been identified in in vitro cell culture systems, including the predicted products of DP-IV hydrolysis.

DP-IV inhibitors have been shown to be efficacious immunosupressants in animal models of transplantation and arthritis. Prodipine (Pro-Pro-diphenyl-phosphonate), an irreversible inhibitor of DP-IV, was shown to double cardiac allograft survival in rats from day 7 to day 14 (Transplantation 63, 1495–1500 (1997)). DP-IV inhibitors have been tested in collagen and alkyldiamine-induced arthritis in rats and showed a statistically significant attenuation of hind paw swelling in this model (Int. J. Immunopharmacology 19, 15–24 (1997), Immunopharmacology 40, 21–26 (1998)). DP-IV is upregulated in a number of autoimmune diseases including rheumatoid arthritis, multiple sclerosis, Graves' disease, and Hashimoto's thyroiditis Immunology Today 20, 367–375 (1999)).

HIV Infection: DP-IV inhibition may be useful for the treatment or prevention of HIV infection or AIDS because a number of chemokines which inhibit HIV cell entry are potential substrates for DP-IV Immunology Today 20, 367–375 (1999)). In the case of SDF-1alpha, cleavage decreases antiviral activity (PNAS 95, 6331–6 (1998)). Thus, stabilization of SDF-1alpha through inhibition of DP-IV would be expected to decrease HIV infectivity.

Hematopoiesis: DP-IV inhibition may be useful for the treatment or prevention of hematopiesis because DP-IV may be involved in hematopoiesis. A DP-IV inhibitor, Val-Boro-Pro, stimulated hematopoiesis in a mouse model of cyclophosphamide-induced neutropenia (WO 99/56753).

Neuronal Disorders: DP-IV inhibition may be useful for the treatment or prevention of various neuronal or psychiatric disorders because a number of peptides implicated in a variety of neuronal processes are cleaved in vitro by DP-IV. A DP-IV inhibitor thus may have a therapeutic benefit in the treatment of neuronal disorders. Endomorphin-2, beta-casomorphin, and substance P have all been shown to be in vitro substrates for DP-IV. In all cases, in vitro cleavage is highly efficient, with $k_{cat}/K_m \sim 10^6$ $M^{-1}s^{-1}$ or greater. In an electric shock jump test model of analgesia in rats, a DP-IV inhibitor showed a significant effect that was independent of the presence of exogenous endomorphin-2 (Brain Research 815, 278–286 (1999)).

Tumor Invasion and Metastasis: DP-IV inhibition may be useful for the treatment or prevention of tumor invasion and metastasis because an increase or decrease in expression of several ectopeptidases including DP-IV has been observed during the transformation of normal cells to a malignant phenotype (J. Exp. Med. 190, 301–305 (1999)). Up- or down-regulation of these proteins appears to be tissue and cell-type specific. For example, increased CD26/DP-IV expression has been observed on T cell lymphoma, T cell acute lymphoblastic leukemia, cell-derived thyroid carcinomas, basal cell carcinomas, and breast carcinomas. Thus, DP-IV inhibitors may have utility in the treatment of such carcinomas.

Benign Prostatic Hypertrophy: DP-IV inhibition may be useful for the treatment of benign prostatic hypertrophy because increased DP-IV activity was noted in prostate tissue from patients with BPH our. J. Clin. Chem. Clin. Biochem. 30, 333–338 (1992)).

Sperm motility/male contraception: DP-IV inhibition may be useful for the altering sperm motility and for male contraception because in seminal fluid, prostatosomes, prostate derived organelles important for sperm motility, possess very high levels of DP-IV activity (Our. J. Clin. Chem. Clin. Biochem 30, 333–338 (1992)).

Gingivitis: DP-IV inhibition may be useful for the treatment of gingivitis because DP-IV activity was found in gingival crevicular fluid and in some studies correlated with periodontal disease severity (Arch. Oral Biol. 37, 167–173 (1992)).

Osteoporosis: DP-IV inhibition may be useful for the treatment or prevention of osteoporosis because GIP receptors are present in osteoblasts.

The subject compounds are further useful in a method for the prevention, treatment, control, amelioration, or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also includes therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of Formula I, and either administered separately or in the same pharmaceutical composition, include, but are not limited to:

(a) other dipeptidyl peptidase IV (DP-IV) inhibitors;

(b) insulin sensitizers including ligands for PPAR receptors (alpha and/or gamma and/or beta-delta) which have activity as agonists, antagonists, selective activators, or partial agonists, including (i) PPARγ agonists such as the glitazones (e.g. troglitazone, pioglitazone, englitazone, MCC-555, rosiglitazone, and the like) and other PPAR ligands, including PPARα/γ dual agonists, such as KRP-297, PPARα agonists such as fenofibric acid derivatives (gemfibrozil, clofibrate, fenofibrate and bezafibrate), and PPARγ partial agonists, (ii) biguanides such as metformin and phenformin, and (iii) protein tyrosine phosphatase-1B (PTP-1B) inhibitors;

(c) insulin or insulin mimetics;

(d) sulfonylureas and other insulin secretagogues such as tolbutamide and glipizide, meglitinide, and related materials;

(e) α-glucosidase inhibitors (such as acarbose);

(f) glucagon receptor antagonists such as those disclosed in WO 98/04528, WO 99/01423, WO 00/39088, and WO 00/69810;

(g) GLP-1, GLP-1 mimetics, GLP-1 receptor agonists, and exendins such as those disclosed in WO00/42026 and WO00/59887;

(h) GIP and GIP mimetics such as those disclosed in WO00/58360, and GIP receptor agonists;

(i) PACAP, PACAP mimetics, and PACAP receptor agonists such as those disclosed in WO 01/23420;

(j) cholesterol lowering agents such as (i) HMG-CoA reductase inhibitors (lovastatin, simvastatin, pravastatin, fluvastatin, atorvastatin, rivastatin, itavastatin, rosuvastatin, and other statins), (ii) sequestrants (cholestyramine, colestipol, and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) PPARα/γ dual agonists, such as KRP-297, (vi) inhibitors of cholesterol absorption, such as beta-sitosterol and ezetimibe, (vii) acyl CoA:cholesterol acyltransferase inhibitors, such as avasimibe, and (viii) anti-oxidants, such as probucol;

(k) PPARδ agonists, such as those disclosed in WO97/28149;

(l) antiobesity compounds such as fenfluramine, dexfenfluramine, phentermine, sibutramine, orlistat, neuropeptide Y5 receptor antagonists, melanocortin 4 receptor agonists, cannabanoid CB-1 receptor antagonists, such as rimonabant, and $\beta_3$ adrenergic receptor agonists;

(m) ileal bile acid transporter inhibitors;

(n) antihypertensives including those acting on the angiotensin or renin systems, such as angiotensin converting enzyme inhibitors, angiotensin II receptor antagonists or renin inhibitors, such as captopril, cilazapril, enalapril, fosinopril, lisinopril, quinapril, ramapril, zofenopril, candesartan, cilexetil, eprosartan, irbesartan, losartan, tasosartan, telmisartan, and valsartan; and (o) agents intended for use in inflammatory conditions such as aspirin, non-steroidal anti-inflammatory drugs, glucocorticoids, azulfidine, and cyclo-oxygenase 2 selective inhibitors.

The above combinations include combinations of a compound of the present invention not only with one other active compound, but also with two or more other active compounds. Non-limiting examples include combinations of compounds having Formula I with two or more active compounds selected from biguanides, sulfonylureas, HMG-CoA reductase inhibitors, PPAR agonists, PTP-1B inhibitors, other DP-IV inhibitors, and anti-obesity compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouth washes and gargles.)

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require inhibition of dipeptidyl peptidase-IV enzyme activity an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

When treating, preventing, controlling, ameliorating, or reducing the risk of diabetes mellitus and/or hyperglycemia or hypertriglyceridemia or other diseases for which compounds of the present invention are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made according to procedures known in the art or as illustrated herein.

The compounds of the present invention can be prepared from beta amino acid intermediates such as those of formula II and substituted heterocyclic intermediates such as those of formula III, using standard peptide coupling conditions followed by deprotection. The preparation of these intermediates is described in the following schemes,

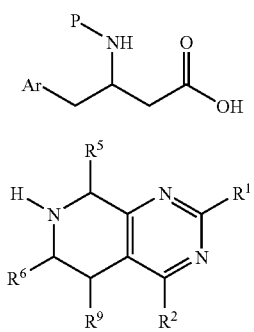

where Ar, $R^1$, $R^2$, $R^5$, $R^6$ and $R^9$ are as defined above and P is a suitable nitrogen protecting group such as tert-butoxycarbonyl, benzyloxycarbonyl, or 9-fluorenylmethoxycarbonyl (Fmoc).

SCHEME 1

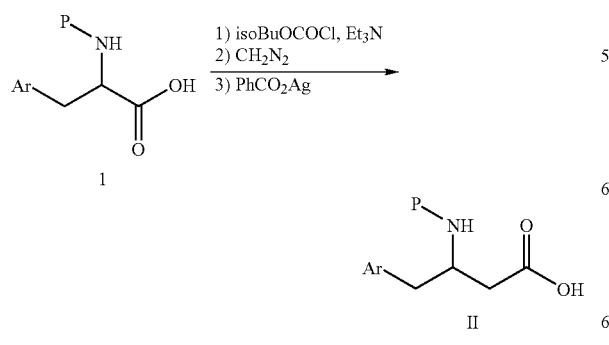

Compounds of formula II are commercially available, known in the literature or may be conveniently prepared by a variety of methods familiar to those skilled in the art. One common route is illustrated in Scheme 1. Acid 1, which may be commercially available or readily prepared from the corresponding amino acid by protection using, for example, di-tert-butyl dicarbonate (for P=Boc), carbobenzyloxy chloride (for P=Cbz), or N-(9-fluorenylmethoxycarbonyloxy) succinimide (for P=Fmoc), is treated with isobutyl chloroformate and a base such as triethylamine or diisopropylethylamine, followed by diazomethane. The resultant diazoketone is then treated with silver benzoate in a solvent such as methanol or aqueous dioxane and may be subjected to sonication following the procedure of Sewald et al., *Synthesis*, 837 (1997) in order to provide the beta amino acid II. As will be understood by those skilled in the art, for the preparation of enantiomerically pure beta amino acids II, enantiomerically pure alpha amino acids 1 may be used. Alternate routes to these compounds can be found in the following reviews: E. Juaristi, *Enantioselective Synthesis of β-Amino Acids*, Ed., Wiley-VCH, New York: 1997, Juaristi et al., *Aldrichimica Acta*, 27, 3 (1994), Cole et al., *Tetrahedron*, 32, 9517 (1994).

SCHEME 2

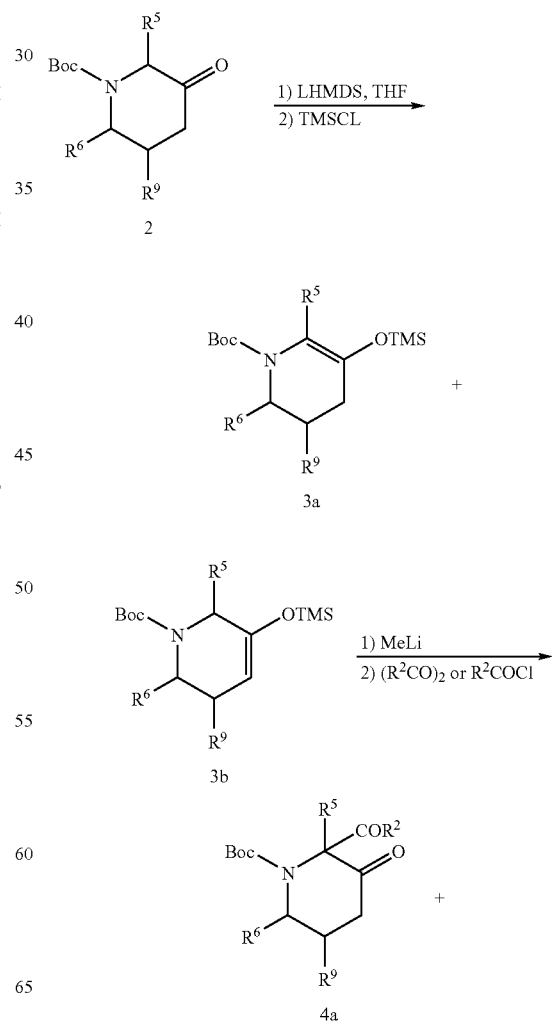

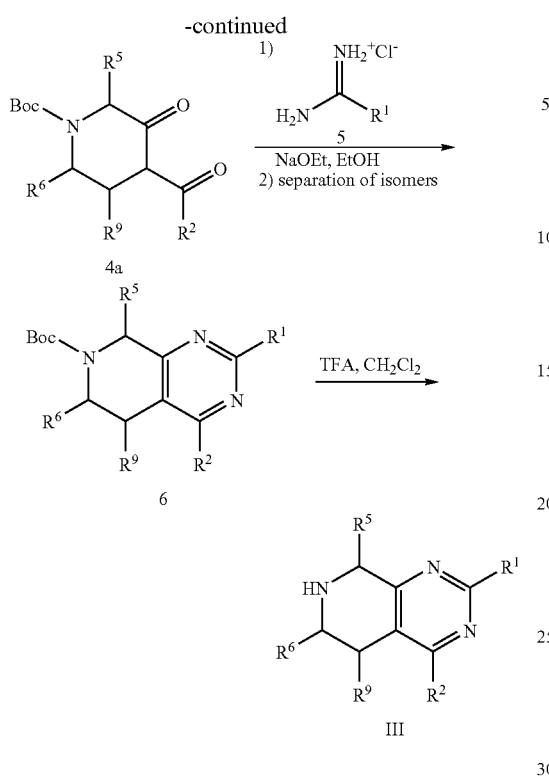

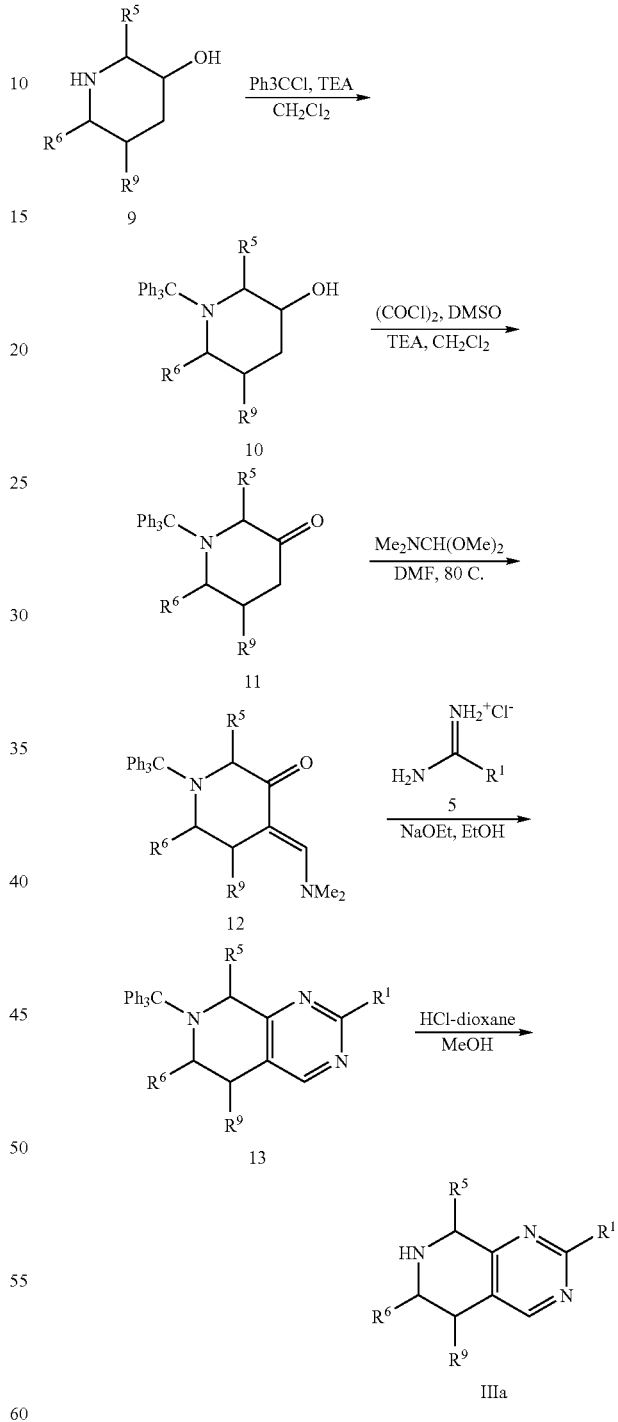

Compounds III are commercially available, known in the literature or may be conveniently prepared by a variety of methods familiar to those skilled in the art. One convenient method is shown in Scheme 2. N-Boc 3-piperidinone 2 is enolized with a base such as LHMDS at low temperature, e.g., −78° C., and the resultant enolate mixture is trapped by treatment with silyl chloride to give a mixture of silyl ethers 3a and 3b. Treatment with methyllithium followed by an acid anhydride or acid chloride provides the beta-diketones 4a and 4b. The mixture may be separated, or conveniently, used directly in the next step. Treatment with amidine 5 in the presence of a base such as sodium ethoxide provides the Boc protected tetrahydropyridopyrimidine 6, following removal of the undesired isomer, for example by chromatographic purification. The protecting group may be removed by treatment with TFA in dichloromethane to give the desired product III.

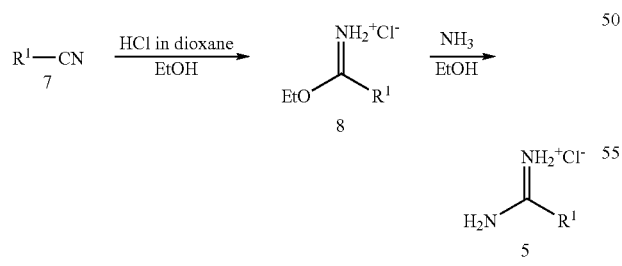

3-Oxopiperidine 1 and amidine 5 are commercially available, known in the literature or may be conveniently prepared by a variety of methods familiar to those skilled in the art. One convenient method for preparation of amidine 5 is shown in Scheme 3. Nitrile 7, which itself is commercially available, known in the literature, or conveniently prepared by a variety of methods familiar to those skilled in the art, is treated with hydrogen chloride, conveniently as a solution in dioxane, in ethanol to give imidate 8. Treatment with an ethanolic ammonia solution provides amidine 5.

Compounds IIIa wherein $R^2$ is H may be conveniently prepared as shown in Scheme 4. 3-Hydroxypiperidine 9 is protected, for example, as its N-trityl derivative by treatment with trityl chloride and a base such as triethylamine to provide 10. Oxidation, conveniently using Swern conditions, gives 3-piperidinone 11. Treatment with 1,1- dimethoxy-N,N-dimethylmethanamine in DMF at elevated temperature gives enamine 12, which is condensed with amidine 5 in the presence of a base such as sodium ethoxide in ethanol to provide pyrimidine 13. Deprotection, in the case of trityl, with an acid such as hydrogen chloride gives tetrahydropyridopyrimidine IIIa.

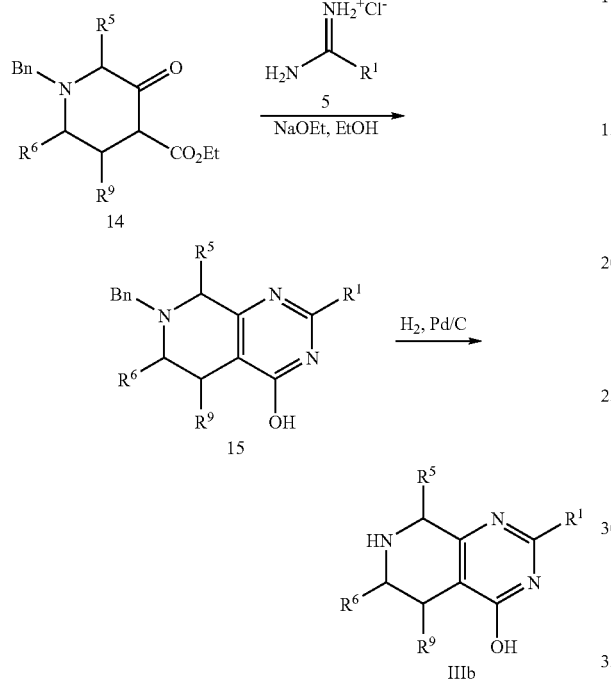

The preparation of intermediate IIIb wherein $R^2$ is OH is illustrated in Scheme 5. Ketoester 14 is treated with amidine 5 in the presence of a base such as sodium ethoxide in ethanol to provide tetrahydropyridopyridimine 15. Deprotection of the nitrogen using catalytic hydrogenation, for example by treatment with hydrogen in the presence of palladium on carbon, provides IIIb.

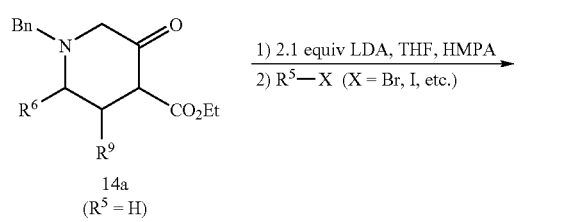

Intermediate 14 from Scheme 5 is commercially available, known in the literature or may be conveniently prepared by a variety of methods familiar to those skilled in the art. One convenient method for preparation of 14 wherein $R^5$ is not H is illustrated in Scheme 6. Intermediate 14a ($R^5$=H) is treated with excess base, for example lithium diisopropylamide at a low temperature, conveniently −78° C., in a solvent such as THF with added HMPA to form the dianion. This is alkylated by treatment with an alkyl halide such as an alkyl bromide or alkyl iodide to provide intermediate 14.

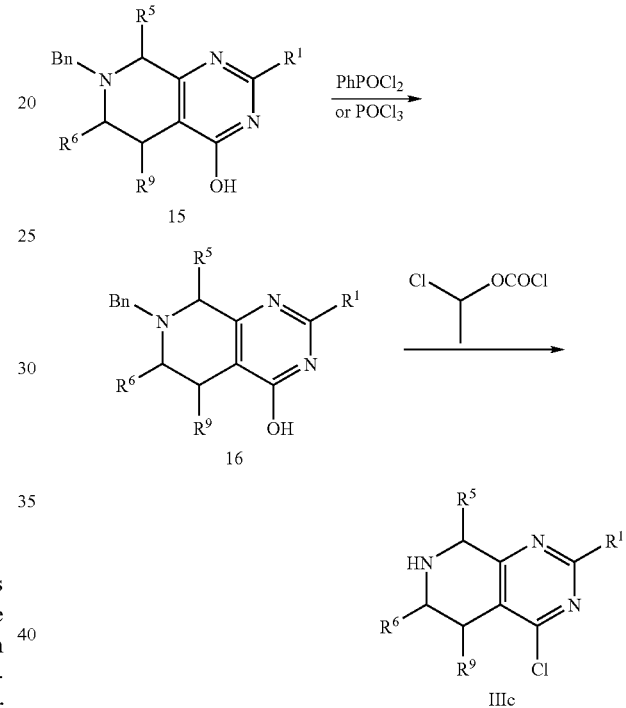

The preparation of intermediate IIIc wherein $R^2$ is Cl is illustrated in Scheme 7. Tetrahydropyridopyridimine 15, prepared as described in Scheme 5, is treated with a chlorinating agent such as phenylphosphonic dichloride or phosphorus oxychloride, typically at elevated temperatures such as 100–200° C., to give chloropyrimidine 16. Deprotection of the nitrogen using 1-chloroethyl chloroformate provides IIIc.

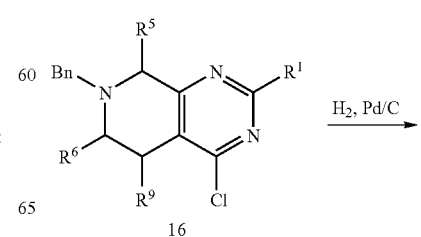

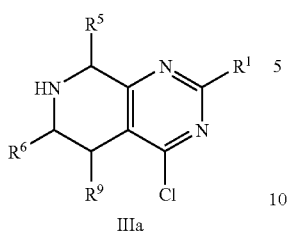

IIIa

An alternate method for the preparation of intermediate IIIa wherein $R^2$ is H is illustrated in Scheme 8. Deprotection of intermediate 16, prepared as described in Scheme 7, using catalytic hydrogenation, for example by treatment with hydrogen in the presence of palladium on carbon, provides IIIa.

SCHEME 9

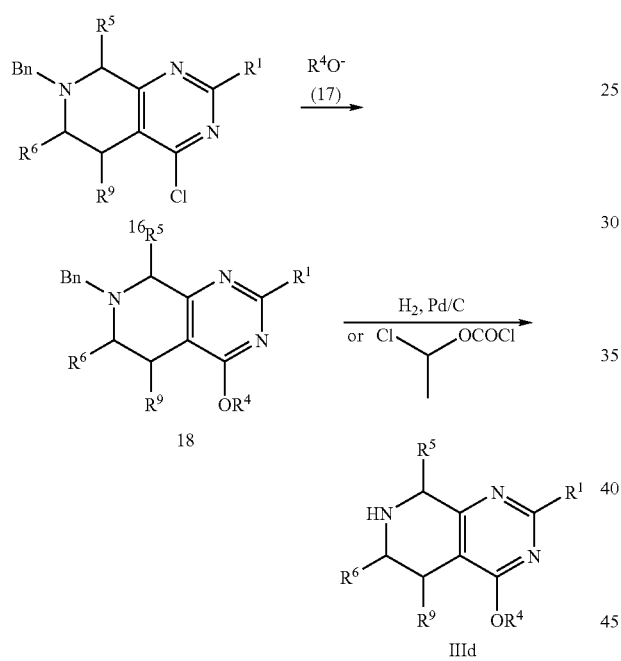

18

IIId

Intermediate IIId wherein $R^2$ is alkoxy ($OR^4$) may be prepared as illustrated in Scheme 9. Chloropyrimidine 16 is treated with alkoxide anion 17, for example sodium methoxide ($R^4$=Me) or sodium ethoxide ($R^4$=Et), to provide ether 18. Deprotection either using catalytic hydrogenation or 1-chloroethyl chloroformate gives the desired tetrahydropyridopyrimidine IIId.

SCHEME 10

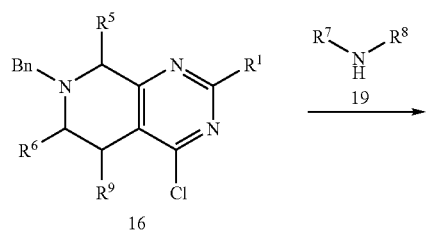

16

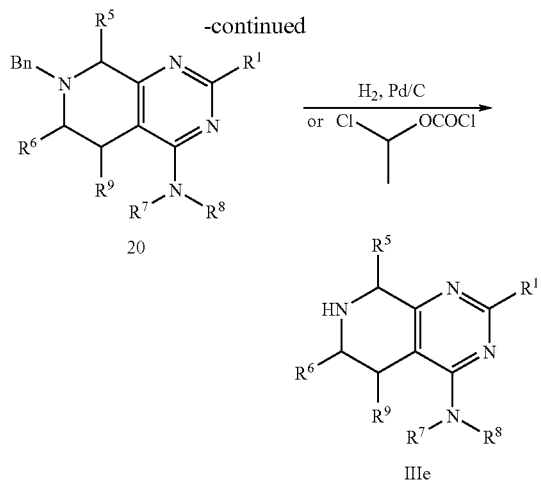

20

IIIe

Intermediate IIIe wherein $R^2$ is an amino group ($NR^7R^8$) may be prepared as illustrated in Scheme 10. Chloropyrimidine 16 is treated with ammonia or a primary or secondary amine 19 to provide amine 20. Deprotection either using catalytic hydrogenation or 1-chloroethyl chloroformate gives the desired tetrahydropyridopyrimidine IIIe.

SCHEME 11

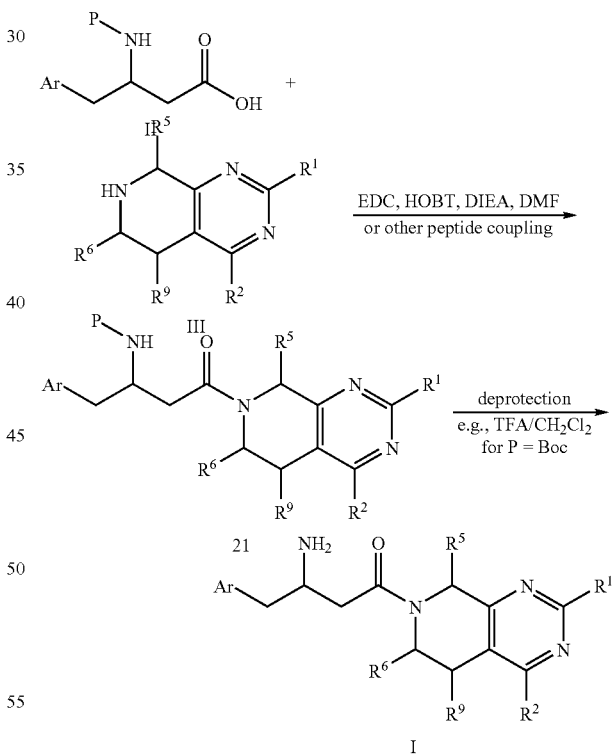

21

I

Intermediates II and III are coupled under standard peptide coupling conditions, for example, using 1-ethyl-3-(3-dimethylaminopropyl)carbodiimide (EDC), 1-hydroxybenzotriazole (HOBT), and a base, generally diisopropylethylamine, in a solvent such as N,N-dimethylformamide (DMF) or dichloromethane for 3 to 48 hours at ambient temperature to provide intermediate 21 as shown in Scheme 11. The protecting group is then removed with, for example, trifluoroacetic acid or methanolic hydrogen chloride in the case of Boc to give the desired amine I. The product is purified from unwanted side products, if necessary, by recrystallization, trituration, preparative thin layer chromatography, flash chromatography on silica gel, or HPLC. Compounds that are purified by HPLC may be isolated as the corresponding salt. Purification of intermediates is achieved in the same manner.

SCHEME 12

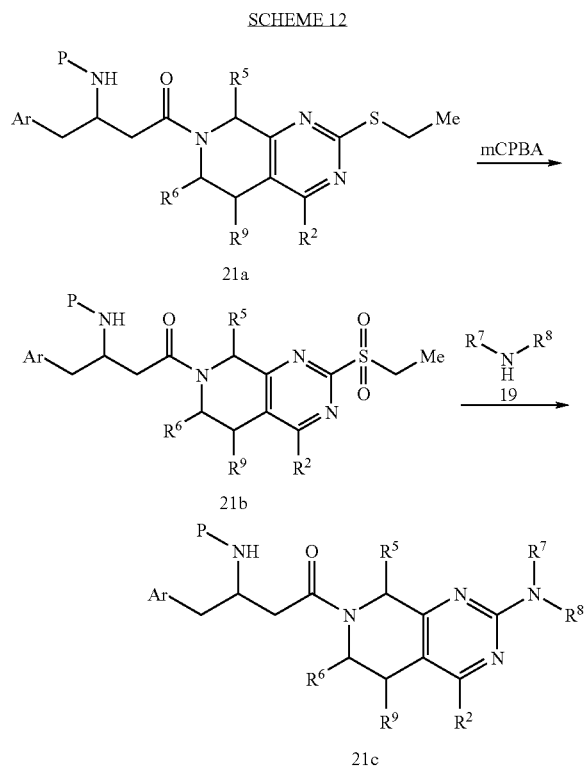

In some cases the intermediate 21 from the coupling reaction described in Scheme 11 may be further modified before removal of the protecting group, for example, by manipulation of substituents on Ar, $R^1$, $R^2$, $R^5$, $R^6$ or $R^9$. These manipulations may include, but are not limited to, reduction, oxidation, alkylation, acylation, and hydrolysis reactions which are commonly known to those skilled in the art. One such example is illustrated in Scheme 12. Intermediate 21a ($R^1$=SEt) is oxidized with meta-chloroperbenzoic acid to provide sulfone 21b. The sulfone may then be displaced with nucleophiles such as ammonia or primary or secondary amine 19 to provide the aminopyrimidine derivatives 21c, which are then deprotected as described in Scheme 11.

SCHEME 13

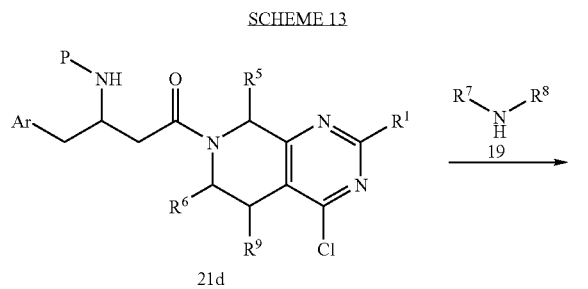

Another such example is illustrated in Scheme 13. Intermediate 21d ($R^2$=Cl) is treated with a nucleophile such as ammonia or primary or secondary amine 19 to provide the aminopyrimidine derivative 21e, which is then deprotected as described in Scheme 11.

SCHEME 14

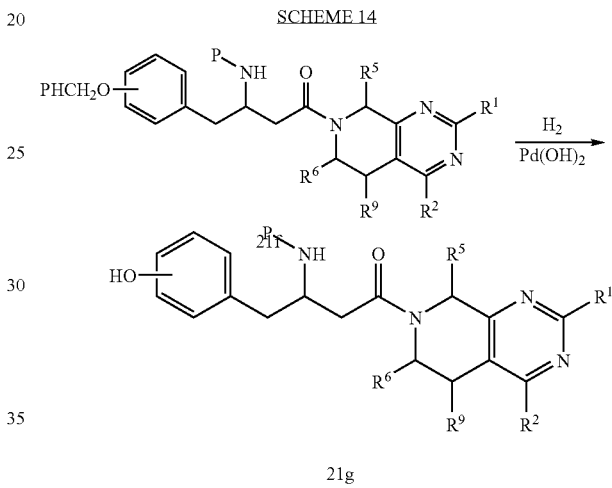

An additional example is provided in Scheme 14. Intermediate 21f ($R^3$=benzyloxy) is treated with hydrogen in the presence of a catalyst such as palladium hydroxide to provide the phenol 21g, which may then be deprotected as described in Scheme 11.

In some cases the final product I from Scheme 11 may be further modified, for example, by manipulation of substituents on Ar, $R^1$, $R^2$, $R^5$, $R^6$ or $R^9$. These manipulations may include, but are not limited to, reduction, oxidation, alkylation, acylation, and hydrolysis reactions which are commonly known to those skilled in the art.

In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

INTERMEDIATE 1

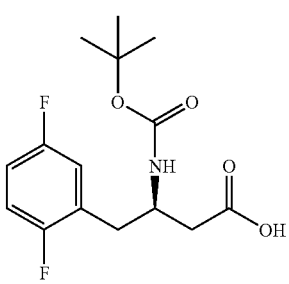

(3R)-3-[(1,1-Dimethylethoxycarbonyl)amino]-4-(2,5-difluorophenyl)butanoic acid

Step A. (R,S)-N-(1,1-Dimethylethoxycarbonyl)-2,5-difluorophenylalanine

To a solution of 0.5 g (2.49 mmol) of 2,5-difluoro-DL-phenylalanine in 5 mL of tert-butanol were added sequentially 1.5 mL of 2N aqueous sodium hydroxide solution and 543 mg of di-tert-butyl dicarbonate. The reaction was stirred at ambient temperature for 16 h and diluted with ethyl acetate. The organic phase was washed sequentially with 1N hydrochloric acid and brine, dried over magnesium sulfate and concentrated in vacuo. The crude material was purified by flash chromatography (silica gel, 97:2:1 dichloromethane:methanol:acetic acid) to afford 671 mg of the title compound. MS 302 (M+1).

Step B. (R,S)-3-[(1,1-Dimethylethoxycarbonyl)amino]-1-diazo-4-(2,5-difluorophenyl)butan-2-one To a solution of 2.23 g (7.4 mmol) of (R,S)-N-(1,1-dimethylethoxycarbonyl)-2,5-difluorophenylalanine in 100 mL of diethyl ether at 0° C. were added sequentially 1.37 mL (8.1 mmol) of triethylamine and 0.931 mL (7.5 mmol) of isobutyl chloroformate and the reaction was stirred at this temperature for 15 min. A cooled ethereal solution of diazomethane was then added until the yellow color persisted and stirring was continued for a further 16 h. The excess diazomethane was quenched by dropwise addition of acetic acid, and the reaction was diluted with ethyl acetate and washed sequentially with 5% hydrochloric acid, saturated aqueous sodium bicarbonate solution and brine, dried over magnesium sulfate and concentrated in vacuo. Purification by flash chromatography (silica gel, 4:1 hexane:ethyl acetate) afforded 1.5 g of diazoketone. $^1$H NMR (500 MHz, CDCl$_3$) δ 7.03–6.95 (m, 1H), 6.95–6.88 (m, 2H), 5.43 (bs, 1H), 5.18 (bs, 1H), 4.45 (bs, 1H), 3.19–3.12 (m, 1H), 2.97–2.80 (m, 1H), 1.38 (s, 9H).

Step C. (3R)-3-[(1,1-Dimethylethoxycarbonyl)amino]-4-(2,5-difluorophenyl)butanoic acid To a solution of 2.14 g (6.58 mmol) of (R,S)-3-[(1,1-dimethylethoxycarbonyl)-amino]-1-diazo-4-(2,5-difluorophenyl)butan-2-one dissolved in 100 mL of methanol at −30° C. were added sequentially 3.3 mL (19 mmol) of diisopropylethylamine and 302 mg (1.32 mmol) of silver benzoate. The reaction was stirred for 90 min before diluting with ethyl acetate and washing sequentially with 2N hydrochloric acid, saturated aqueous sodium bicarbonate, and brine. The organic phase was dried over magnesium sulfate, concentrated in vacuo and the enantiomers were separated by preparative chiral HPLC (Chiralpak AD column, 5% ethanol in hexanes) to give 550 mg of the desired (R)-enantiomer, which eluted first. This material was dissolved in 50 mL of a mixture of tetrahydrofuran:methanol: 1N aqueous lithium hydroxide (3:1:1) and stirred at 50° C. for 4 h. The reaction was cooled, acidified with 5% dilute hydrochloric acid and extracted with ethyl acetate. The combined organic phases were washed with brine, dried over magnesium sulfate and concentrated in vacuo to give 360 mg of the title compound as a white foamy solid. $^1$H NMR (500 MHz, CDCl$_3$) δ 7.21 (m, 1H), 6.98 (m, 2H), 6.10 (bs, 1H), 5.05 (m,1H), 4.21 (m, 1H), 2.98 (m, 2H), 2.60 (m, 2H), 1.38 (s, 9H).

INTERMEDIATE 2

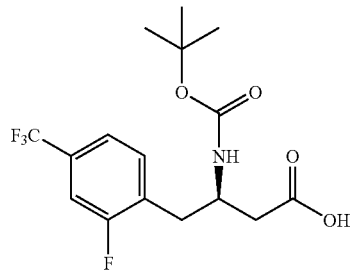

(3R)-3-[(1,1-Dimethylethoxycarbonyl)amino]-4-[2-fluoro-4-(trifluoromethyl)phenyl]-butanoic acid

Step A. (2R,5S)-2,5-Dihydro-3,6-dimethoxy-2-(2'-fluoro-4'-(trifluoromethyl)benzyl)-5-isopropylpyrazine To a solution of 3.32 g (18 mmol) of commercially available (2S)-2,5-dihydro-3,6-dimethoxy-2-isopropylpyrazine in 100 mL of tetrahydrofuran at −70° C. was added 12 mL (19 mmol) of a 1.6M solution of butyllithium in hexanes. After stirring at this temperature for 20 min, 5 g (19.5 mmol) of 2-fluoro-4-trifluoromethylbenzyl bromide in 20 mL of tetrahydrofuran was added and stirring was continued for 3 h before warming the reaction to ambient temperature. The reaction was quenched with water, concentrated in vacuo, and extracted with ethyl acetate. The combined organic phase was washed with brine, dried, and concentrated in vacuo. Purification by flash chromatography (silica gel, 0–5% ethyl acetate in hexanes) afforded 5.5 g of the title compound. $^1$H NMR (500 MHz, CDCl$_3$) δ 7.33–7.25 (m, 3H), 4.35–4.31 (m, 1H), 3.75 (s, 3H), 3.65 (s, 3H), 3.60 (t, 1H, J=3.4 Hz), 3.33 (dd, 1H, J=4.6, 13.5 Hz), 3.03 (dd, 1H, J=7, 13.5 Hz), 2.25–2.15 (m, 1H), 1.0 (d, 3H, J=7 Hz), 0.66 (d, 3H, J=7 Hz).

Step B. (R)-N-(1,1-Dimethylethoxycarbonyl)-2-fluoro-4-(trifluoromethyl)phenylalanine methyl ester To a solution of 5.5 g (15 mmol) of (2R,5S)-2,5-dihydro-3,6-dimethoxy-2-(2'-fluoro-4'-(trifluoromethyl)benzyl)-5-isopropylpyrazine in 50 mL of a mixture of acetonitrile: dichloromethane (10:1) was added 80 mL of 1N aqueous trifluoroacetic acid. The reaction was stirred for 6 h and the organic solvents were removed in vacuo. Sodium carbonate was added until the solution was basic (>pH 8), and then the reaction was diluted with 100 mL of tetrahydrofuran and 10 g (46 mmol) of di-tert-butyl dicarbonate was added. The resulting slurry was stirred for 16 h, concentrated in vacuo, and extracted with ethyl acetate. The combined organic phase was washed with brine, dried, and concentrated in vacuo. Purification by flash chromatography (silica gel, 20% ethyl acetate in hexanes) afforded 5.1 g of the title compound. $^1$H NMR (500 MHz, CDCl$_3$) δ 7.38–7.28 (m, 3H), 5.10 (bd, 1H), 4.65–3.98 (m, 1H), 3.76 (s, 3H), 3.32–3.25 (m, 1H), 3.13–3.05 (m, 1H), 1.40 (s, 9H).

Step C. (R)-N-(1,1-Dimethylethoxycarbonyl)-2-fluoro-4-(trifluoromethyl)phenylalanine A solution of 5.1 g (14 mmol) of (R,S)-N-(1,1-dimethylethoxycarbonyl)-2-fluoro-4-(trifluoromethyl)phenylalanine methyl ester in 350 mL of a mixture of tetrahydrofuran:methanol:1N lithium hydroxide (3:1:1) was stirred at 50° C. for 4 h. The reaction was cooled, acidified with 5% dilute hydrochloric acid and extracted with ethyl acetate. The combined organic phases were washed with brine, dried over magnesium sulfate and concentrated in vacuo to give 4.8 g of the title compound. $^1$H NMR (500 MHz, CD$_3$OD) δ 7.45–7.38 (m, 3H), 4.44–4.40 (m, 1H), 3.38–3.33 (m, 1H), 2.98 (dd, 1H, J=9.6, 13.5 Hz), 1.44 (s, 9H).

Step D. (3R)-3-[(1,1-Dimethylethoxycarbonyl)amino]-4-[2-fluoro-4-(trifluoromethyl)phenyl]butanoic acid To a solution of 3.4 g (9.7 mmol) of the product from Step C in 60 mL of tetrahydrofuran at 0° C. were added sequentially 2.3 mL (13 mmol) of diisopropylethylamine and 1.7 mL (13 mmol) of isobutyl chloroformate and the reaction was stirred at this temperature for 30 min. A cooled ethereal solution of diazomethane was then added until the yellow color persisted and stirring was continued for a further 16 h. The excess diazomethane was quenched by dropwise addition of acetic acid, and the reaction was diluted with ethyl acetate and washed sequentially with 5% hydrochloric acid, saturated aqueous sodium bicarbonate solution and brine, dried over magnesium sulfate and concentrated in vacuo. Purification by flash chromatography (silica gel, 9:1 hexane:ethyl acetate) afforded 0.5 g of diazoketone. To a solution of 0.5 g (1.33 mmol) of the diazoketone dissolved in 100 mL of methanol at 0° C. were added sequentially 0.7 mL (4 mmol) of diisopropylethylamine and 32 mg (0.13 mmol) of silver benzoate. The reaction was stirred for 2 h before diluting with ethyl acetate and washing sequentially with 2N hydrochloric acid, saturated aqueous sodium bicarbonate, and brine. The organic phase was dried over magnesium sulfate, concentrated in vacuo and dissolved in 50 mL of a mixture of tetrahydrofuran:methanol:1N aqueous lithium hydroxide (3:1:1) and stirred at 50° C. for 3 h. The reaction was cooled, acidified with 5% dilute hydrochloric acid and extracted with ethyl acetate. The combined organic phases were washed with brine, dried over magnesium sulfate and concentrated in vacuo to give 410 mg of the title compound as a white foamy solid. $^1$H NMR (500 MHz, CD$_3$OD) δ 7.47–7.33 (m, 3H), 4.88 (bs, 1H), 4.26–3.98 (m, 1H), 3.06–3.01 (m, 1H), 2.83–2.77 (m, 1H), 2.58–2.50 (m, 2H), 1.29 (s, 9H).

INTERMEDIATE 3

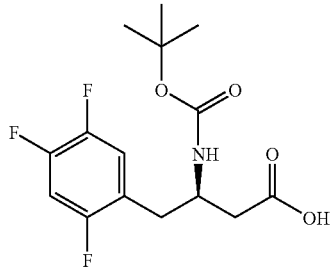

(3R)-3-[(1,1-Dimethylethoxycarbonyl)amino]-4-(2,4,5-trifluorophenyl)butanoic acid

Step A. (2S,5R)-2,5-Dihydro-3,6-dimethoxy-2-isopropyl-5-(2',4',5'-trifluorobenzyl)pyrazine The title compound (3.81 g) was prepared from 3.42 g (18.5 mmol) of (2S)-2,5-dihydro-3,6-dimethoxy-2-isopropylpyrazine and 5 g (22.3 mmol) of 2,4,5-trifluorobenzyl bromide using the procedure described for Intermediate 2, Step A. $^1$H NMR (500 MHz, CDCl$_3$) δ 7.01 (m, 1H), 6.85 (m, 1H), 4.22 (m, 1H), 3.78 (m, 3H), 3.64 (m, 3H), 3.61 (m, 1H), 3.20 (m, 1H), 2.98 (m, 1H), 2.20 (m, 1H), 0.99 (d, 3H, J=8 Hz), 0.62 (d, 3H, J=8 Hz).

Step B. (R)-N-(1,1-Dimethylethoxycarbonyl)-2,4,5-trifluorophenylalanine methyl ester To a solution of 3.81 g (11.6 mmol) of (2S,5R)-2,5-dihydro-3,6-dimethoxy-2-isopropyl-5-(2',4',5'trifluoro-benzyl)pyrazine in 20 mL of acetonitrile was added 20 mL of 2N hydrochloric acid. The reaction was stirred for 72 h and concentrated in vacuo. The residue was dissolved in 30 mL of dichloromethane and 10 mL (72 mmol) of triethylamine and 9.68 g (44.8 mmol) of di-tert-butyldicarbonate were added. The reaction was stirred for 16 h, diluted with ethyl acetate and washed sequentially with 1N hydrochloric acid and brine. The organic phase was dried over sodium sulfate, concentrated in vacuo and purified by flash chromatography (silica gel, 9:1 hexanes:ethyl acetate) to afford 2.41 g of the title compound. $^1$H NMR (500 MHz, CDCl$_3$) δ 6.99 (m, 1H), 6.94 (m, 1H), 5.08 (m, 1H), 4.58 (m, 1H), 3.78 (m, 3H), 3.19 (m, 1H), 3.01 (m, 1H), 1.41 (s, 9H).

Step C. (R)-N-(1,1-Dimethylethoxycarbonyl)-2,4,5-trifluorophenylalanine

The title compound (2.01 g) was prepared from 2.41 g (7.5 mol) of (R)-N-(1,1-dimethylethoxycarbonyl)-2,4,5-trifluorophenylalanine methyl ester using the procedure described for Intermediate 2, Step C. LC-MS 220.9 (M+1-BOC).

Step D. (3R)-3-[(1,1-Dimethylethoxycarbonyl)amino]-4-(2,4,5-trifluorophenyl)butanoic acid To a solution of 0.37 g (1.16 mmol) of (R)-N-(1,1-dimethylethoxycarbonyl)-2,4,5-trifluorophenylalanine in 10 mL of diethyl ether at −20° C. were added sequentially 0.193 mL (1.3 mmol) of triethylamine and 0.18 mL (1.3 mmol) of isobutyl chloroformate, and the reaction was stirred at this temperature for 15 min. A cooled ethereal solution of diazomethane was then added until the yellow color persisted and stirring was continued for a further 1 h. The excess diazomethane was quenched by dropwise addition of acetic acid, and the reaction was diluted with ethyl acetate and washed sequentially with saturated aqueous sodium bicarbonate solution and brine, dried over magnesium sulfate and concentrated in vacuo. Purification by flash chromatography (silica gel, 3:1 hexane:ethyl acetate) afforded 0.36 g of diazoketone. To a solution of 0.35 g (1.15 mmol) of the diazoketone dissolved in 12 mL of 1,4-dioxane: water (5:1) was added 26 mg (0.113 mmol) of silver benzoate. The resultant solution was sonicated for 2 h before diluting with ethyl acetate and washing sequentially with 1N hydrochloric acid and brine, drying over magnesium sulfate and concentrating in vacuo. Purification by flash chromatography (silica gel, 97:2:1 dichloromethane:methanol:acetic acid) afforded 401 mg of the title compound. $^1$H NMR (500 MHz, CDCl$_3$) δ 7.06 (m, 1H), 6.95 (m, 1H), 5.06 (bs, 1H), 4.18 (m, 1H), 2.98 (m, 2H), 2.61 (m, 2l), 1.39 (s, 9H).

INTERMEDIATE 4

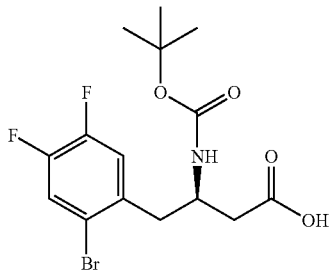

(3R)-4-(2-Bromo-4,5-difluorophenyl)-3-[(1,1-dimethylethoxycarbonyl)amino]butanoic acid To a solution of 2.4 g (10 mmol) of 2-bromo-4,5-difluorobenzoic acid (prepared according to the procedure of Braish et al., *Synthetic Commun.*, pg 3067–3074, 1992) in 75 mL of tetrahydrofuran was added 2.43 g (15 mmol) of carbonyldiimidazole. The solution was heated under reflux for 3.5 h, cooled to ambient temperature and 0.38 g (10 mmol) of sodium borohydride in 15 mL of water was added. The reaction was stirred for 10 min and partitioned between ethyl acetate and 10% aqueous sodium bicarbonate solution. The organic layer was washed twice with warm water, brine, dried over magnesium sulfate, and concentrated in vacuo. Purification by flash chromatography (silica gel, 4:1 hexane:ethyl acetate) afforded 1.9 g of 2-bromo-4,5-difluorobenzyl alcohol. To a solution of 1.9 g (8.4 mmol) of 2-bromo-4,5-difluorobenzyl alcohol in 30 mL of dichloromethane at 0° C. was added 3.4 g (10 mmol) of carbon tetrabromide and 2.7 g (10 mmol) of triphenylphosphine. The reaction was stirred for 2 h at this temperature, the solvent was removed in vacuo and the residue stirred with 100 mL of diethyl ether. The solution was filtered, concentrated in vacuo, and purified by flash chromatography (silica gel, 20:1 hexane:ethyl acetate) to afford 2.9 g of 2-bromo-4,5-difluorobenzyl bromide contaminated with carbon tetrabromide which was used without further purification. Using the procedures outlined for the preparation of Intermediates 2 and 3, the benzyl bromide derivative was converted to the title compound: LC-MS 394 and 396 (M+1).

Essentially following the procedures outlined for the preparation of Intermediates 1–4, the Intermediates in Table 1 were prepared.

TABLE 1

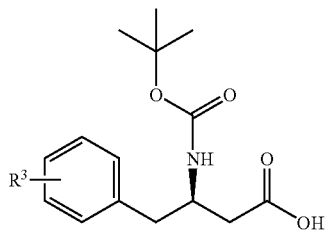

| Intermediate | R³ | Selected ¹H NMR data (CD₃OD) |
|---|---|---|
| 5 | 2-F, 4-Cl, 5-F | 7.11 (dd, 1H, J = 8.9, 6.4 Hz), 7.03 (dd, 1H, J = 9.0, 6.6) |
| 6 | 2-F, 5-Cl | 7.27 (dd, 1H, J = 6.4, 2.5 Hz), 7.21 (m, 1H), 7.03 (t, 1H, J = 9.2 Hz) |

TABLE 1-continued

| Intermediate | R³ | Selected ¹H NMR data (CD₃OD) |
|---|---|---|
| 7 | 2-Me, 5-Cl | 7.16 (d, 1H, J = 1.8 Hz), 7.11–7.07 (m, 2H), 2.34 (s, 3H) |
| 8 | 2-Cl, 5-Cl | 7.34 (d, 1H, J = 9.0), 7.33 (d, 1H, J = 2.1 Hz), 7.21 (dd, 1H, J = 8.5, 2.5 Hz) |
| 9 | 2-F, 3-Cl, 6-F | 7.35 (td, 1H, J = 8.5, 5.8 Hz), 6.95 (t, 1H, J = 8.5 Hz) |
| 10 | 3-Cl, 4-F | 7.33 (d, 1H, J = 6.9 Hz), 7.19–7.11 (m, 2H) |
| 11 | 2-F, 3-F, 6-F | 7.18–7.12 (m, 1H), 6.91 (m, 1H) |
| 12 | 2-F, 4-F, 6-F | 6.81 (t, 2H, J = 8.4 Hz) |
| 13 | 2-OCH₂Ph, 5-F | 7.49 (d, 2H, J = 7.6 Hz), 7.38 (t, 2H, J = 7.3 Hz), 7.30 (t, 1H, J = 7.3 Hz), 6.96–6.89 (m, 3H), 5.11 (d, 1H, J = 11.7 Hz), 5.08 (d, 1H, J = 11.9 Hz) |

EXAMPLE 1

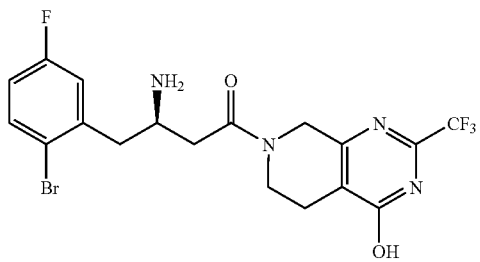

7-[(3R)-3-Amino-4-(2,5-difluorophenyl)butanoyl]-2-(trifluoromethyl)-5,6,7,8-tetrahydropyrido[3,4-d]pyrimidin-4-ol Step A. 7-(Phenylmethyl)-2-(trifluoromethyl)-5,6,7,8-tetrahydropyrido[3,4-d]pyrimidin-4-ol To a solution of sodium ethoxide, prepared from 3.2 g (133 mmol) of sodium metal and 200 mL of absolute ethanol, at ambient temperature was added 8.3 g (74 mmol) of trifluoroacetamidine followed by 17.8 g (60 mmol) of ethyl 1-benzyl-3-oxopiperidinecarboxylate hydrochloride in portions over 15 min. The reaction mixture was stirred at ambient temperature for 1 h, then heated at reflux for 30 h. The mixture was concentrated in vacuo. The resultant red foam was partitioned between 300 mL of 1 N aqueous sodium hydroxide solution and 300 mL of ether. The aqueous layer was washed with 300 mL of ether and the combined ether phases were extracted with 50 mL of 1 N aqueous sodium hydroxide solution. The combined aqueous phases were cooled in an ice-water bath and neutralized to pH 7 with concentration hydrochloric acid. The solids were collected, washed with water, and dried in vacuo to give 13.99 (75%) of beige solid, which was used as is. An analytical sample was prepared by recrystallization of 200 mg from isopropanol to give 157 mg of a white powder. LC-MS 310.0 (M+1).

Step B. 2-(Trifluoromethyl)-5,6,7,8-tetrahydropyrido[3,4-d]pyrimidin-4-ol, acetic acid salt A mixture of 160 mg (0.52 mmol) of benzylamine from Step A, 5 mL of acetic acid and ~50 mg of 5% Pd/C was shaken on a Parr apparatus under 40 psi of hydrogen for 5 h. The reaction was judged to be 80–90% complete by LC-MS analysis. An additional ~20 mg of 5% Pd/C was added and the reaction was shaken under 40 psi of hydrogen for 3 h. The reaction mixture was filtered and concentrated. The resultant solid was triturated with ether twice and dried in vacuo to give 118 mg (81%) of the title compound. LC-MS 220.0 (M+1).

Step C. 7-[(3R)-3-Amino-4-(2,5-difluorophenyl) butanoyl]-2-(trifluoromethyl)-5,6,7,8-tetrahydropyrido[3,4-d]pyrimidin-4-ol A suspension of 30 mg (0.10 mmol) of (3R)-3-[(1,1-dimethylethoxycarbonyl)amino]4-(2,5-difluorophenyl)butanoic acid, 34 mg (0.12 mmol) of amine from Step B, 25 mg (0.12 mmol) of ethyl dimethylaminopropylcarbodiimide (EDC), and 18 mg (0.12 mmol) of hydroxybenzotriazole (HOBt) in 1.0 mL of dichloromethane was treated with 0.050 mL of diisopropylethylamine. The reaction mixture was sonicated for 5 min, then shaken for 3 days at ambient temperature. The mixture was diluted with 1 mL of dichloromethane, treated with 2 mL of trifluoroacetic acid (TFA), and concentrated in vacuo. Purification by HPLC (YMC C18 Pro column, gradient elution, 10–90% MeCN:H$_2$O containing 0.1% TFA) gave 40 mg of a viscous gum which was converted to free base on a 1-g SCX column to provide 25 mg of a white solid. The solid was triturated with ether, collected and dried under vacuo to give 21.2 mg of the title compound as a white powder. LC-MS 417.1 (M+1).

EXAMPLE 2

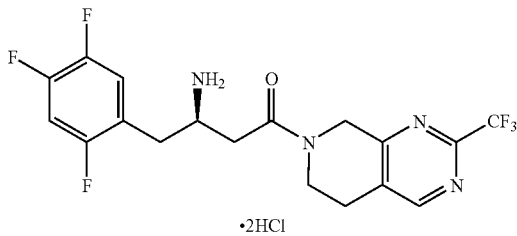

7-[(3R)-3-Amino-4-(2,4,5-trifluorophenyl)butanoyl]-2-(trifluoromethyl)-5,6,7,8-tetrahydropyrido[3,4-d]pyrimidine, dihydrochloride

Step A. 4-Chloro-7-(phenylmethyl)-2-(trifluoromethyl)-5,6,7,8-tetrahydropyrido[3,4-d]pyrimidine A mixture of 29.6-g (95.7 mmol) of 7-(phenylmethyl)-2-(trifluoromethyl)-5,6,7,8-tetrahydropyrido[3,4-d]pyrimidin-4-ol (prepared essentially as described in Example 1, Step A) and 53 mL of phenylphosphonic dichloride in a 250-mL round bottom flask was heated at 150° C. After 2 h, the reaction was judged to be complete by TLC analysis. The mixture was cooled to ambient temperature and poured onto 400 g of ice, transferring with ~500 mL of ethyl acetate. The aqueous layer was neutralized with solid sodium bicarbonate and the layers separated. The aqueous layer was extracted with two portions of ethyl acetate. The combined organics were washed sequentially with saturated aqueous sodium bicarbonate solution and brine, dried over sodium sulfate and concentrated to give a brown solid. The solid was boiled in 2 L of hexane with charcoal, filtered, and concentrated in vacuo to give 23.9 g (76%) of the title compound as a yellow solid. LC-MS 328.3 (M+1).

Step B. 2-(Trifluoromethyl)-5,6,7,8-tetrahydropyrido[3,4-d]pyrimidine, hydrochloride A flask containing a solution of 23.4 g (71.41 mmol) of amine from Step A in 285 mL of ethyl acetate and 530 mL of methanol was purged with nitrogen, and 2 g of 10% Pd/C was added. The mixture was stirred under 1 atm of hydrogen until the reaction was judged complete by TLC analysis (~7.5 h total). The mixture was filtered through Celite, and the Celite washed with methanol. The organics were concentrated in vacuo and the resultant pale yellow oil was triturated with 400 mL of ether. Crystals formed and an additional 400 mL of ether was added. The mixture was stirred overnight. The resultant solid was collected by filtration and dried in vacuo to give 16.3 g of off-white crystals that contained an impurity by TLC analysis. The crystals were dissolved in a minimum amount of methanol. Ether was added to turbidity and the mixture was warmed on a steam bath. Crystals formed and the mixture was allowed to cool to ambient temperature and aged for 30 min. It was then filtered. The collected solid was dried in vacuo to give 14.8 g of the title compound as a white crystalline solid. LC-MS 203.8 (M+1).

Step C. 7-[(3R)-3-[(1,1-Dimethylethoxycarbonyl)amino]-4-(2,4,5-trifluorophenyl)butanoyl]-2-(trifluoromethyl)-5,6,7,8-tetrahydropyrido[3,4-d]pyrimidine A 1-L round bottom flask was charged with 15.5 g (46.5 mmol) of (3R)-3-[(1,1-dimethylethoxycarbonyl)amino]4-(2,4,5-trifluorophenyl)butanoic acid and 160 mL of acetonitrile. To the resultant suspension was added 14.5 g (60.5 mmol) of amine hydrochloride from Step B. The mixture was cooled to 5° C. and 12 g (62.8 mmol) of EDC and 6.9 mL (62.8 mmol) of N-methylmorpholine were added. After 2 h, the reaction was judged to be complete by LC-MS analysis. The mixture was partitioned between 100 mL of water and 160 mL of ethyl acetate. The organic phase was washed sequentially with 100 mL of saturated aqueous sodium bicarbonate solution and 100 mL of brine, dried over sodium sulfate, and concentrated in vacuo. Purification by Biotage flash chromatography (silica gel, 30–60% ethyl acetate/hexane) gave 20.3 g of the title compound as a white foam. LC-MS 419.4 (M+1-BOC).

Step D. 7-[(3R)-3-Amino-4-(2,4,5-trifluorophenyl)butanoyl]-2-(trifluoromethyl)-5,6,7,8-tetrahydropyrido[3,4-d]pyrimidine, dihydrochloride A solution of 26.5 g (51.1 mmol) of 7-[(3R)-3-[(1,1-dimethylethoxycarbonyl)amino]-4-(2,4,5-trifluorophenyl)butanoyl]-2-(trifluoromethyl)-5,6,7,8-tetrahydropyrido[3,4-d]pyrimidine in 130 mL of methanol was cooled to 0° C. and 130 mL of 9 N aqueous hydrochloric acid was added. The mixture was allowed to warm to ambient temperature, stirred overnight, and the methanol removed in vacuo. The aqueous residue was neutralized by the addition of sodium hydroxide and extracted with ethyl acetate. The organic phase was washed sequentially with 1 N aqueous sodium hydroxide solution and brine, dried over sodium sulfate and concentrated in vacuo. Purification by Biotage flash chromatography (silica gel, 5–10% methanol/dichloromethane) gave 17.5 g of a brown oil. To a mixture of 16.5 g of this oil in 50 mL of water was added 3.45 mL of concentrated hydrochloric acid. The mixture was stirred vigorously for ~2 h until a solution was formed. The resultant solution was lyophilized overnight, dissolved in ~50 mL of water, and lyophilized again to provide 17.8 g of the title compound as a white solid. LC-MS 419.3 (M+1).

EXAMPLE 3

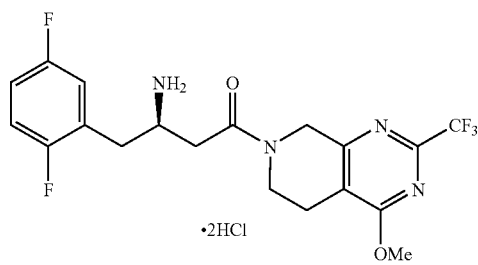

7-[(3R)-3-Amino-4-(2,5-difluorophenyl)butanoyl]-4-methoxy-2-(trifluoromethyl)-5,6,7,8-tetrahydropyrido[3,4-d]pyrimidine, dihydrochloride Step A. 4-Methoxy-7-(phenylmethyl)-2-(trifluoromethyl)-5,6,7,8-tetrahydropyrido[3,4-d]pyrimidine 4-Chloro-7-(phenylmethyl)-2-(trifluoromethyl)-5,6,7,8-tetrahydropyrido[3,4-d]pyrimidine (98 mg, 0.30 mmol) and 1.5 mL of 0.5 M sodium methoxide in methanol was warmed to 60° C. overnight. The mixture was concentrated under nitrogen and partitioned between ether and water. The ether layer was washed with brine, dried and concentrated to give 94 mg of the title compound as a yellow oil. LC-MS 324.0 (M+1).

Step B. 4-Methoxy-2-(trifluoromethyl)-5,6,7,8-tetrahydropyrido[3,4-d]pyrimidine, hydrochloride A solution of 94 mg (0.30 mmol) of the anine from Step A in 1.5 mL of dichloromethane was treated with 0.041 mL (0.375 mmol) of 1-chloroethyl chloroformate. The solution was warmed to 45° C. for 18 h, cooled to room temperature, and concentrated under nitrogen. A 1.5-mL portion of methanol was added and the mixture was warmed to 40° C. for 2 h, cooled, and concentrated under nitrogen and then in vacuo. Trituration with ether followed by drying of the resultant off-white solid in vacuo gave 73 mg (90%) of the title compound. LC-MS 234.2 (M+1).

Step C. 7-[(3R)-3-Amino-4-(2,5-difluorophenyl)butanoyl]-4-methoxy-2-(trifluoromethyl)-5,6,7,8-tetrahydropyrido[3,4-d]pyrimidine, dihydrochloride A mixture of 43 mg (0.13 mmol) of (3R)-3-[(1,1-dimethylethoxycarbonyl)amino]4-(2,5-difluorophenyl)butanoic acid, 35 mg (0.13 mmol) of amine from Step B, 25 mg (0.13 mmol) of EDC, 18 mg (0.13 mmol) of HOBt, and 0.052 mL of diisopropylethylamine in 1.0 mL of dichloromethane was stirred overnight at ambient temperature. The mixture was purified directly by preparative TLC (1 mm silica gel, 35% ethyl acetate/hexane) to give 60 mg of the Boc intermediate. The intermediate was treated with 3 mL of dichloromethane and 2 mL of TFA at room temperature for 1 h. The reaction mixture was concentrated under nitrogen. The resultant TFA salt was converted to the free base on a 1-g SCX column, eluting the product with 1 M ammonia in methanol. The methanol and excess ammonia were removed in vacuo, and the residue was treated with 1 M hydrogen chloride in ethyl acetate and ether was added. Trituration of the product from ether-hexane gave 46.7 mg of the title compound as an off-white powder. LC-MS 431.0 (M+1).

EXAMPLE 4

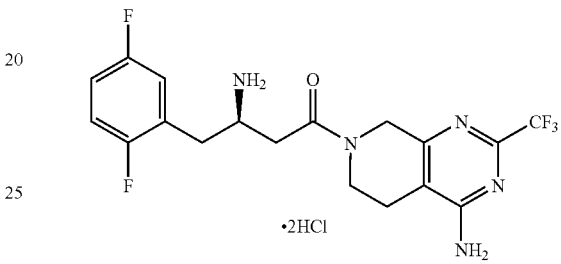

7-[(3R)-3-Amino-4-(2,5-difluorophenyl)butanoyl]-4-amino-2-(trifluoromethyl)-5,6,7,8-tetrahydropyrido[3,4-d]pyrimidine, dihydrochloride Step A. 4-Chloro-2-(trifluoromethyl)-5,6,7,8-tetrahydropyrido[3,4-d]pyrimidine, hydrochloride 4-Chloro-7-(phenylmethyl)-2-(trifluoromethyl)-5,6,7,8-tetrahydropyrido[3,4-d]pyrimidine (262 mg, 0.80 mmol) was debenzylated following a procedure similar to that described in Example 3, Step B. Trituration with ether gave 208 mg (95%) of the title compound as an off-white solid. LC-MS 238.1 (M+1).

Step B. 7-[(3R)-3-[(1,1-Dimethylethoxycarbonyl)amino]-4-(2,5-difluorophenyl)butanoyl]-4-chloro-2-(trifluoromethyl)-5,6,7,8-tetrahydropyrido[3,4-d]pyrimidine A mixture of 60 mg (0.20 mmol) of (3R)-3-[(1,1-dimethylethoxycarbonyl)amino]4-(2,5-difluorophenyl)butanoic acid and 0.033 mL (0.30 mmol) of N-methylmorpholine in 0.6 mL of THF was cooled to −15° C. and 0.031 mL of isobutyl chloroformate was added. After 10 min, 1.0 mL of ether was added. The mixture was transferred to a syringe and filtered through a syringe filter into a mixture of 35 mg (0.20 mmol) of amine hydrochloride from Step A and 0.033 mL (0.30 mmol) of N-methylmorpholine in 0.5 mL of THF at 0° C. The reaction mixture was warmed to ambient temperature. After 30 min, the reaction was judged to be complete by TLC. The mixture was filtered using a syringe filter, washing with ether, and concentrated under nitrogen. The solid was partitioned between ethyl acetate and water. The organics were washed with brine, dried over magnesium sulfate and concentrated to give a yellow oil. Purification by flash chromatography (5 g silica gel cartridge, 10 to 35% ethyl acetate/hexane step gradient) gave 62 mg (58%) of the title compound as a white solid.

Step C. 7-[(3R)-3-Amino-4-(2,5-difluorophenyl)butanoyl]-4-amino-2-(trifluoromethyl)-5,6,7,8-tetrahydropyrido[3,4-d]pyrimidine dihydrochloride A mixture of 62 mg (0.116 mmol) of chloro derivative from Step B and 2 mL of 0.5 M ammonia in THF was heated in a sealed tube at 60° C. for 20 h. The reaction mixture cooled, and concentrated under nitrogen to give 70 mg of Boc intermediate which was deprotected and converted to the hydrochloride salt following a procedure similar to that described for Example 3, Step C. Trituration with ether gave 19.9 mg of the title compound. LC-MS 416.1 (M+1).

EXAMPLE 5

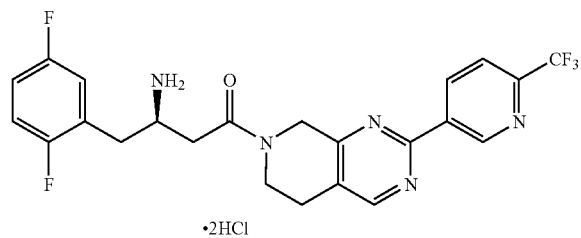

7-[(3R)-3-Amino-4-(2,5-difluorophenyl)butanoyl]-2-[6-(trifluoromethyl)pyrin-3-yl]-5,6,7,8-tetrahydropyrido[3,4-d]pyrimidine, dihydrochloride Step A. 7-Benzyl-2-[6-(trifluoromethyl)pyridin-3-yl]-5,6,7,8-tetrahydropyrido[3,4-d]pyrimidin-4-ol A mixture of 258 mg (11.2 mmol) of sodium in 10 mL of absolute ethanol was stirred at ambient temperature for 1 h. To the resultant sodium ethoxide solution was added 893 mg (3.0 mmol) of ethyl 1-benzyl-3-oxopiperidine-4-carboxylate hydrochloride in portions followed by 840 mg (3.72 mmol) of 6-(trifluoromethyl)pyridine-3-amidine hydrochloride. The reaction mixture was heated at reflux for 18 h, then concentrated in vacuo. To the residue was added ~30 mL of 1N aqueous sodium hydroxide solution and 15 mL of water to give an insoluble solid and a yellow solution. The solid was filtered off and washed with water to provide 496 mg of the title compound. The aqueous filtrate was acidified to ~pH 5 with concentrated hydrochloric acid and the solid precipitate was collected to give an additional 334 mg of the title compound as a bright yellow powder (72% total yield). LC-MS 387.2 (M+1).

Step B. 7-Benzyl-4-chloro-2-[6-(trifluoromethyl)pyridin-3-yl]-5,6,7,8-tetrahydropyrido[3,4-d]pyrimidine A mixture of 232 mg (0.6 mmol) of 7-benzyl-2-[6-(trifluoromethyl)pyridin-3-yl]-5,6,7,8-tetrahydropyrido[3,4-d]pyrimidin-4-ol from Step A and 1.0 mL of phosphorous oxychloride in a 25-mL round bottom flask was treated with 90 mg (0.095 mL, 0.6 mmol) of N,N-diethylaniline. The mixture was warmed to 110° C. After 4 h, it was cooled to ambient temperature and concentrated in vacuo. Water (15–20 mL) was added. The mixture was neutralized by the addition of solid sodium bicarbonate and extracted with 2 portions of ethyl acetate. The combined organic phases were washed with brine, dried, and concentrated. Purification by flash chromatography (silica gel, 0 to 20% ethyl acetate/hexane step gradient) gave 220 mg of a light yellow oil. LC-MS 405.2 (M+1).

Step C. 2-[6-(Trifluoromethyl)pyridin-3-yl]-5,6,7,8-tetrahydropyrido[3,4-d]pyrimidine, hydrochloride A mixture of 220 mg of 7-benzyl-4-chloro-2-[6-(trifluoromethyl)pyridin-3-yl]-5,6,7,8-tetrahydropyrido[3,4-d]pyrimidine and 40–50 mg of 10% palladium on carbon in 8 mL of methanol and 5 mL of ethyl acetate was stirred under 1 atm of hydrogen for 3 h. The mixture was filtered and concentrated to give a yellow solid. Trituration with ether gave 120 mg of the title compound as an off-white powder. LC-MS 281.1 (M+1).

Step D. 7-[(3R)-3-Amino-4-(2,5-difluorophenyl)butanoyl]-2-[6-(trifluoromethyl)pyridin-3-yl]-5,6,7,8-tetrahydropyrido[3,4-d]pyrimidine, dihydrochloride A mixture of 60 mg (0.20 mmol) of (3R)-3-[(1,1-dimethylethoxycarbonyl)amino]-4-(2,5-difluorophenyl)butanoic acid and 0.033 mL (0.30 mmol) of N-methylmorpholine in 0.6 mL of THF was cooled to −15° C. and 0.031 mL (0.24 mmol) of isobutyl chloroformate was added. After 10 min, 1.0 mL of dry ether was added. After 2 min, the mixture was transferred to a syringe and filtered through a syringe filter into a mixture of 63 mg (0.20 mmol) of 2-[6-(trifluoromethyl)pyridin-3-yl]-5,6,7,8-tetrahydropyrido[3,4-d]pyrimidine hydrochloride and 0.033 mL (0.30 mmol) of N-methylmorpholine in 0.8 mL of THF at 0° C. The reaction mixture was warmed to ambient temperature. After 30 min, the mixture was concentrated in vacuo. After attempted trituration proved problematic, purification by flash chromatography (5 g silica gel cartridge, 15 to 50% ethyl acetate/hexane step gradient) gave 68 mg of the Boc protected intermediate. This was treated with TFA in methanol at ambient temperature for 1 h and concentrated. The product was converted to free base on a 1 g SCX column, eluting the product with 1 M ammonia in methanol. The hydrochloride salt was formed by treatment with 1 M hydrogen chloride in ethyl acetate. Trituration with ether gave 47 mg of the title compound as a light yellow powder. LC-MS 478.2 (M+H).

EXAMPLE 6

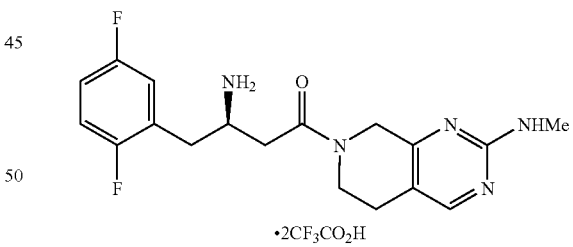

7-[(3R)-3-Amino-4-(2,5-difluorophenyl)butanoyl]-N-methyl-5,6,7,8-tetrahydropyrido[3,4-d]pyrimidin-2-amine, bis(trifluoroacetic acid) salt Step A. 3-Hydroxy-1-(triphenylmethyl)piperidine To a stirred suspension of 1.37 g (10.0 mmol) of 3-hydroxypiperidine hydrochloride and 2.53 g (3.5 mL) of triethylamine in 30 mL of dichloromethane at 0° C. was added dropwise 2.93 g (10.5 mmol) of trityl chloride. The mixture was stirred at ambient temperature overnight, diluted with 100 mL of dichloromethane, washed sequentially with water, 5% aqueous citric acid solution, saturated sodium bicarbonate solution, and brine, dried over sodium sulfate, and concentrated to give 3.85 g of the title compound as a white foam.

Step B. 1-Tritylpiperidin-3-one

To a solution of 1.7 mL (24 mmol) of DMSO in 30 mL of dichloromethane at −50° C. was added dropwise 5.5 mL (11.0 mmol) of 2.0 M oxalyl chloride solution in dichloromethane. After 10 min, a solution of 3.85 g (10.0 mmol) of 3-hydroxy-1-(triphenylmethyl)piperidine from Step A in 15 mL of dichloromethane was added dropwise. After 15 min, 7.0 mL (50 mmol) of triethylamine was added dropwise. The reaction mixture was allowed to warm to ambient temperature over 0.5 h. The mixture was diluted with dichloromethane, washed sequentially with water, 5% aqueous citric acid solution, saturated sodium bicarbonate solution, and brine, dried over sodium sulfate and concentrated. Purification by flash chromatography (silica gel, 6% ethyl acetate/hexane) gave 1.95 g (57%) of the title compound as a white crystalline solid.

Step C. 4-[(Dimethylamino)methylene]-1-tritylpiperidin-3-one

A mixture of 1.94 g (5.68 mmol) of piperidinone from Step B in 10 mL of DMF was treated with 0.677 g (0.755 mL) of 1,1-dimethoxy-N,N-dimethylmethylamine. The colorless suspension was warmed to 80° C. under nitrogen. After 18 h, the mixture was cooled to ambient temperature and concentrated in vacuo. The dark red residue was partitioned between ethyl acetate and water. The organic layer was washed with brine, dried over magnesium sulfate and concentrated to give 2.25 g of a pale yellow-orange foam. Crystallization of a 2.03-g portion from ether (2 crops) gave a total of 1.17 g (52%) of the title compound.

Step D. 2-(Ethylthio)-7-trityl-5,6,7,8-tetrahydropyrido[3,4-d]pyrimidine

A 148-mg (0.80 mmol) portion of ethyl imidothiocarbamate hydrobromide in 1.5 mL of absolute ethanol was treated with 0.30 mL of 2.68 M sodium ethoxide solution in ethanol. After 10 min, 158 mg (0.40 mmol) of ketone from Step C in 0.5 mL of ethanol was added. The reaction flask was sealed under nitrogen and warmed at 80° C. overnight, then concentrated under nitrogen and in vacuo. The residue was partitioned between ethyl acetate and water. The organic later was concentrated to give 200 mg of a red-orange gum. Purification by preparative TLC (silica gel, 15% ethyl acetate/hexane) gave 81 mg (41%) of the title compound as an off-white foam.

Step E. 2-(Ethylthio)-5,6,7,8-tetrahydropyrido[3,4-d]pyrimidine, hydrochloride

A suspension of 81 mg (0.185 mmol) of trityl compound from Step D in 0.5 mL of methanol was treated with 4 N hydrogen chloride solution in dioxane. The reaction mixture was stirred at ambient temperature for 2 h, then concentrated under nitrogen and then in vacuo. Trituration with ether gave 47 mg (~100%) of the title compound as a pale yellow solid.

Step F. 7-[(3R)-3-[(1,1-Dimethylethoxycarbonyl)amino]-4-(2,5-difluorophenyl)butanoyl]-2-(ethylthio)-5,6,7,8-tetrahydropyrido[3,4-d]pyrimidine A mixture of 47 mg (0.19 mmol) of 2-(ethylthio)-5,6,7,8-tetrahydropyrido[3,4-d]pyrimidine hydrochloride, 59 mg (0.19 mmol) of (3R)-3-[(1,1-dimethylethoxycarbonyl)amino]-4-(2,5-difluorophenyl)butanoic acid, 37 mg (0.19 mmol) of EDC, 26 mg (0.19 mmol) of HOBt, and 0.15 mL (0.57 mmol) of diisopropylethylamine in 1.5 mL of dichloromethane was stirred at ambient temperature overnight. The mixture was subjected directly to purification by flash chromatography (5 g silica gel cartridge, 20-to-50% ethyl acetate/hexane step gradient) to give 85 mg (91%) of the title compound as a white solid.

Step G. 7-[(3R)-3-[(1,1-Dimethylethoxycarbonyl)amino]-4-(2,5-difluorophenyl)butanoyl]-2-(ethylsulfonyl)-5,6,7,8-tetrahydropyrido[3,4-d]pyridine Thioether from Step F (85 mg, 0.173 mmol) in 1.5 mL of THF was cooled to 0° C. and 75 mg (0.367 mmol) of m-chloroperbenzoic acid was added in one portion. After 10 min, the reaction mixture was warmed to ambient temperature, stirred for 1.5 h, and concentrated under nitrogen. The residue was partitioned between ethyl acetate and saturated aqueous sodium bicarbonate solution to give 105 mg of crude product. Purification by flash chromatography (2-g silica gel cartridge, 50% then 100% ethyl acetate/hexane) gave 70 mg (77%) of the title compound as a white foam.

Step H. 7-[(3R)-3-Amino-4-(2,5-difluorophenyl)butanoyl]-N-methyl-5,6,7,8-tetrahydropyrido[3,4-d]pyrimidin-2-amine, bis(trifluoroacetic acid) salt Sulfone (36 mg, 0.069 mmol) from Step G and 1.0 mL of 2.0 M methylamine solution in THF were sealed under nitrogen and warmed at 65° C. overnight. The mixture was cooled, concentrated under nitrogen, and purified by preparative TLC (silica gel, 5% methanol/dichloromethane) to give 24.2 mg (76%) of the Boc intermediate. Deprotection was achieved by treatment with 3 mL of TFA in 5 mL of dichloromethane at ambient temperature. Once the reaction was judged to be complete, the mixture was concentrated. The residue was dissolved in ethyl acetate and concentrated to remove excess TFA. Trituration with ether gave 24 mg of the title compound as a pale yellow powder. LC-MS 362.1 (M+1).

EXAMPLE 7

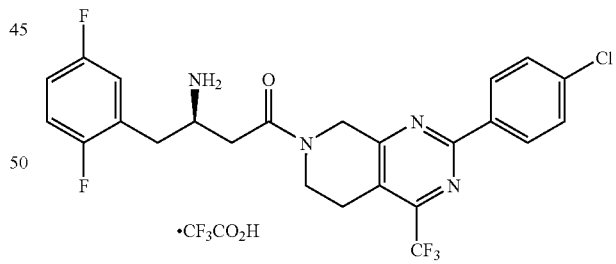

7-[(3R)-3-Amino-4-(2,5-difluorophenyl)butanoyl]-2-(4-chlorophenyl)-4-(trifluoromethyl)-5,6,7,8-tetrahydropyrido[3,4-d]pyrimidine, trifluoroacetic acid salt Step A. tert-Butyl 5-[(trimethylsilyl)oxy]-3,4-dihydropyridine-1(2H)-carboxylate and tert-Butyl 5-[(trimethylsilyl)oxy]-3,6-dihydropyridine-1(2H)-carboxylate To a solution of 115 mL of 1.0 M THF solution of lithium hexamethyldisilyl amide in 290 mL of anhydrous THF in a dried 1-L round bottom flask under nitrogen at −78° C. was added dropwise a solution of 20 g (0.1004 mmol) of tert-butyl 3-oxopiperidine-1-carboxylate in 150 of THE via canula over a 1-h period. The reaction mixture was stirred at −78° C. for 50 min, then 18 mL (1.4 equiv) of trimethylsilyl choride was added in portions. The mixture was stirred 30 min, warmed to ambient temperature and stirred an additional 30 min, then concentrated to a small volume in vacuo at 25° C. It was partitioned between hexane and 1:1 water: saturated aqueous sodium carbonate solution. The aqueous phase was extracted with two portions of hexane. The combined organics were washed with brine, dried over sodium sulfate, and concentrated at 25° C. in vacuo to give 31.87 g of the title compounds as a yellow oil.

Step B. tert-butyl 3-oxo-4-(trifluoroacetyl)piperidine-1-carboxylate and tert-butyl 3-oxo-2-(trifluoroacetyl)piperidine-1-carboxylate To a dried 100-mL round bottom flask was added 11.5 mL of methyllithium (1.6 M solution in ether). The ether was removed in vacuo and the flask charged with 40 mL of dry THF. The mixture was cooled to −15° C. and a solution of 5.0 g (18.42 mmol) of enol ethers from Step A in 40 mL of dry THF was added. The mixture was stirred at −15° C. for an additional 40 min, cooled to −78° C., and transferred slowly via cannula over 30 min to a solution of 2.6 mmol of trifluoroacetic anhydride in 100 mL of dry THF. The mixture was stirred at −78° C. for an additional 1 h, then quenched by the addition of 5 mL of saturated aqueous ammonium chloride solution, warmed to room temperature, and concentrated in vacuo. The residue was partitioned between ethyl acetate and water. The organics were concentrated to give 6.1 g of an orange oil. Purification by flash chromatography (silica gel, eluting sequentially with 20%, 40% and 60% ethyl acetate/hexane) gave 1.91 g of the title compound (5:1 isomeric mixture) as an orange oil.

Step C. tert-butyl 2-(4-chlorophenyl)-4-(trifluoromethyl)-5,8-dihydropyrido[3,4-d]pyrimidine-7(6H)-carboxylate A solution of 144 mg (0.51 mmol) of 4-chlorobenzamidine in 0.5 mL of absolute ethanol was treated with 0.229 mL of sodium ethoxide solution (21 wt. % in ethanol) and stirred at ambient temperature for 10 min. The resultant orange solution was treated with 100 mg (0.34 mmol) of the mixture of diketones from Step B in a total of 0.8 mL of absolute ethanol. The reaction mixture was stirred at ambient temperature for 20 min, then warmed to 80° C. overnight, cooled and concentrated. The residue was partitioned between ethyl acetate and water. The organic phase was washed with brine, dried over sodium sulfate, and concentrated to give 170 mg of an orange semisolid. Trituration with 5 mL of ether gave 150 mg of an orange, viscous oil. Purification by flash chromatography (silica gel, eluting sequentially with 0, 10, and 20% ethyl acetate/hexane) gave 34 mg of the title compound as the faster eluting isomer.

Step D. 2-(4-chlorophenyl)-4-(trifluoromethyl)-5,6,7,8-tetrahydropyrido[3,4-d]pyrimidine, trifluoroacetic acid salt The compound from Step C (34 mg) in 3 mL of dichloromethane and 3 mL of TFA was shaken and kept at ambient temperature for 45 min. The mixture was concentrated under nitrogen and then in vacuo. Trituration with ether gave 35 mg of the title compound as a white solid. LC-MS 314.0 (M+1).

Step E. 7-[(3R)-3-Amino-4-(2,5-difluorophenyl) butanoyl]-2-(4-chlorophenyl)-4-(trifluoromethyl)-5,6,7,8-tetrahydropyrido[3,4-d]pyrimidine, trifluoroacetic acid salt A mixture of 28 mg (0.09 mmol) of (3R)-3-[(1,1-dimethylethoxycarbonyl)amino]-4-(2,5-difluorophenyl)butanoic acid, 35 mg (0.082 mmol) of amine from Step D, 17 mg of EDC, 12 mg of HOBt, and 0.075 mL of diisopropylethylamine in 1.0 mL of dichloromethane was kept at ambient temperature for 18 h. The mixture was applied directly to a 5-g silica gel cartridge, which was then eluted sequentially with 20 and 35% ethyl acetate/hexane to give 36 mg of the Boc protected intermediate. This was treated with 3 mL of TFA in 6 mL of dichloromethane for 1 h at ambient temperature. The mixture was concentrated under a stream of nitrogen and then in vacuo. The residue was triturated with ether to give, after drying in vacuo, 40.5 mg of the title compound as a white solid. LC-MS 510.9 (M+1).

EXAMPLE 8

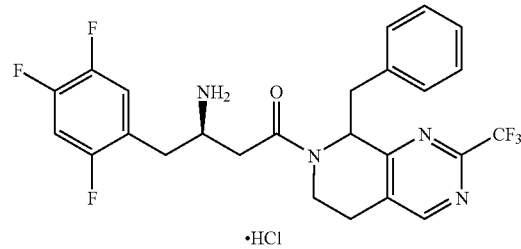

7-[(3R)-3-Amino-4-(2,4,5-trifluorophenyl)butanoyl]-2-(trifluoromethyl)-8-benzyl-5,6,7,8-tetrahydropyrido[3,4-d]pyrimidine, hydrochloride Step A. Ethyl 1,2-dibenzyl-3-oxopiperidine-4-carboxylate To a solution of 3.7 mL (26.6 mmol) of diisopropylethylamine in 55 mL of dry THF at −78° C. was added dropwise n-butyllithium (25 mmol, 10.0 mL of a 2.5 M solution in hexanes). The bath was replaced with an ice-water bath. After 20 min, the mixture was recooled to −78° C. and 3.10 g (11.86 mmol) of ethyl 1-benzyl-3-oxopiperidine-4-carboxylate in a mixture of 20 mL of THF and 4.4 mL (24.4 mmol) of HMPA was added dropwise. After 2 h, 1.47 mL (12.4 mmol) of benzyl bromide was added dropwise, and the resultant mixture was allowed to warm slowly to ambient temperature overnight. The reaction was then quenched by the addition of 5 mL of saturated aqueous ammonium chloride solution. THF was removed in vacuo, and the residue was partitioned between ether and water. The organic phase was washed with 2 portions of brine and concentrated to give a red oil. Purification by Biotage chromatography (silica gel, 3% ethyl acetate/hexane) gave 1.96 g (47%) of the title compound as a light yellow mobile oil. LC-MS 352.1 (M+1).

Step B. 7,8-Dibenzyl-2-(trifluoromethyl)-5,6,7,8-tetrahydropyrido[3,4-d]pyrimidin-4-ol A 3.4 mL aliquot of sodium ethoxide solution in ethanol, prepared from 1.24 g of sodium and 23.6 mL of absolute ethanol, was treated with 1.00 g (8.93 mmol) of trifluoroacetamidine in 3 mL of absolute ethanol followed by 1.06 g (3.01 mmol) of ketoester from Step A in 8 mL of absolute ethanol. The reaction mixture was stirred at ambient temperature for 15 min, then warmed at 87° C. in a sealed tube. After 18 h, the reaction was cooled, and an additional 3.4 mL of the sodium ethoxide solution and 1.00 g of trifluoroacetamidine were added. The mixture was heated at 87° C. for an additional 24-h period, then cooled and concentrated. The residue was partitioned between ether and 0.5 N aqueous sodium hydroxide solution. The aqueous phase was extracted with ether and then acidified with concentrated hydrochloric acid and extracted with ether. All the ether extracts were combined, washed with brine, and concentrated to give 1.73 g of a yellow semisolid. Purification by flash chromatography (silica gel, 3.5% methanol/dichloromethane) gave 1012 mg (84%) of a yellow solid. Trituration with methanol gave 784 mg of the title compound as a bright yellow solid. LC-MS 400.2 (M+1).

Step C. 7,8-Dibenzyl-4-chloro-2-(trifluoromethyl)-5,6,7,8-tetrahydropyrido[3,4-d]pyrimidine A mixture of 669 mg (1.68 mmol) of 7,8-dibenzyl-2-(trifluoromethyl)-5,6,7,8-tetrahydropyrido[3,4-d]pyrimidin-4-ol and 1.2 mL of phenylphosphonic dichloride was heated in a sealed tube at 150° C. for 2.5 h. The mixture was cooled to ~100° C., then poured into crushed ice, washing with ethyl acetate. The resultant biphasic mixture was neutralized with solid sodium bicarbonate to ~pH 8 with vigorous stirring. The ethyl acetate layer was removed. The aqueous layer was extracted with ethyl acetate. The combined organic phases were washed sequentially with saturated aqueous sodium bicarbonate solution and brine, dried, and concentrated to give a red, viscous oil. Purification by Biotage chromatography (silica gel, 5% ethyl acetate/hexane) gave 464 mg (66%) of the title compound as a yellow solid. LC-MS 418.0 (M+1).

Step D. 8-Benzyl-2-(trifluoromethyl)-5,6,7,8-tetrahydropyrido[3,4-d]pyrimidine, hydrochloride A mixture of 420 mg (1.005 mmol) of 7,8-dibenzyl-4-chloro-2-(trifluoromethyl)-5,6,7,8-tetrahydropyrido[3,4-d] pyrimidine from Step C and 63 mg of 10% palladium on carbon in 4 mL of ethyl acetate and 7 mL of methanol was stirred under an atmosphere of hydrogen for 2 h. The mixture was filtered through a 0.45 micron syringe filter, washing with methanol, and concentrated to give a white solid. Trituration with ether gave 330 mg (100%) of the title compound as a white powder. LC-MS 294.1 (M+1).

Step E. 7-[(3R)-3-[(1,1-Dimethylethoxycarbonyl) amino]-4-(2,4,5-trifluorophenyl)butanoyl]-2-(trifluoromethyl)-8-benzyl-5,6,7,8-tetrahydropyrido[3,4-d] pyrimidine A mixture of 133 mg (0.40 mmol) of (3R)-3-[(1,1-dimethylethoxycarbonyl)amino]-4-(2,4,5-trifluorophenyl) butanoic acid and 162 mg (0.50 mmol) of 8-benzyl-2-(trifluoromethyl)-5,6,7,8-tetrahydropyrido[3,4-d] pyrimidine, hydrochloride in 1.5 mL of acetonitrile at 0° C. was treated sequentially with 81 mg (0.42 mmol) of EDC and 0.047 mL (0.42 mmol) of N-methyl morpholine. After 10 min, the mixture was warmed to ambient temperature and stirred for 3 h, then partitioned between 10 mL of ethyl acetate and 4 mL of water. The organic layer was washed sequentially with saturated aqueous sodium bicarbonate solution and brine, dried and concentrated to give 281 mg of the title compound as a mixture of diastereomers. Purification by flash chromatography (silica gel, 10 to 35% ethyl acetate/hexane) followed by HPLC on a Chiralpak AD column (9% ethanol/hexane) gave 51 mg of the faster eluting isomer and 47 mg of the slower eluting isomer.

Step F. 7-[(3R)-3-Amino-4-(2,4,5-trifluorophenyl) butanoyl]-2-(trifluoromethyl)-8-benzyl-5,6,7,8-tetrahydropyrido[3,4-d]pyrimidine, hydrochloride The individual isomers from Step D (25 mg and 29 mg, respectively) were treated separately with 4 M hydrogen chloride solution in dioxane at ambient temperature for 2 h. Concentration under nitrogen, then in vacuo, followed by trituration with ether and drying gave 21.6 and 30.5 mg, respectively, of the title compound as two individual diastereomers. LC-MS 509.1 (M+1) and 509.1 (M+H), respectively.

EXAMPLE 9

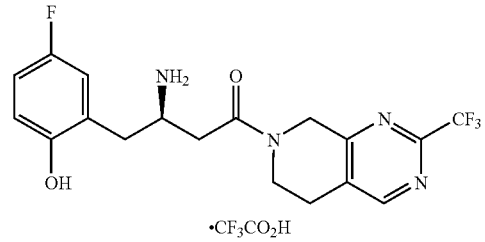

·CF₃CO₂H

7-[(3R)-3-Amino-4-(2-hydroxy-5-fluorophenyl)butanoyl]-2-(trifluoromethyl)-5,6,7,8-tetrahydropyrido [3,4-d]pyrimidine, trifluoroacetic acid salt Step A. 7-[(3R)-3-[(1,1-Dimethylethoxycarbonyl) amino]-4-(2-benzyloxy-5-fluorophenyl)butanoyl]-2-(trifluoromethyl)-5,6,7,8-tetrahydropyrido[3,4-d] pyrimidine A mixture of 363 mg (0.9 mmol) of (3R)-3-[(1,1-dimethylethoxycarbonyl)amino]4-(2-benzyloxy-5-fluorophenyl) butanoic acid, 72 mg (0.3 mmol) of 2-(trifluoromethyl)-5,6,7,8-tetrahydropyrido[3,4-d]pyrimidine hydrochloride, 0.174 mL (1.0 mmol) of diisopropylethylamine, 136 mg (1.0 mmol) of 1-hydroxy-7-azabenzotriazole (HOAT) and 380 mg (1.0 mmol) of O-(7-azabenzotriazol-1-yl)-N,N,N',N'-tetramethyluronium hexafluorophosphate (HATU) in 5 mL of dichloromethane was stirred under an atmosphere of nitrogen overnight. The reaction mixture was diluted with 100 mL of ethyl acetate, washed sequentially with 5% hydrochloric acid, saturated aqueous sodium bicarbonate solution, and brine, dried over magnesium sulfate, and concentrated. Purification by preparative TLC (silica gel, 70% ethyl acetate/hexane) gave 152 mg (86%) of the title compound.

Step B. 7-[(3R)-3-Amino-4-(2-hydroxy-5-fluorophenyl)butanoyl]-2-(trifluoromethyl)-5,6,7,8-tetrahydropyrido[3,4-d]pyrimidine, trifluoroacetic acid salt A 38.3 mg (0.1 mmol) portion of BOC protected benzyl ether from Step A in 5:2:1 ethyl acetate/methanol/dichloromethane was stirred over palladium hydroxide under an atmosphere of hydrogen for 1.5 h. The mixture was filtered through a pad of Celite and concentrated to give the BOC protected phenol, which was treated with 1:1 TFA/dichloromethane for 1 h. Concentration and purification by HPLC (YMC C18 Pro column, gradient elution, 10–90% MeCN:H$_2$O containing 0.1% TFA) gave the title compound. LC-MS 399.3 (M+1).

Essentially following the procedures outlined for Examples 1–9, the compounds listed of Table 2 were prepared.

TABLE 2

| Ex. | R$^1$ | R$^2$ | R$^3$ | R$^5$ | MS (M + 1) |
|---|---|---|---|---|---|
| 10 | CF$_3$ | H | 2-F, 5-F | H | 401.0 |
| 11 | CF$_3$ | H | 2-F, 5-Cl | H | 417.1 |
| 12 | CF$_3$ | H | 2-Cl, 5-Cl | H | 435.4 |
| 13 | CF$_3$ | H | 2-Me, 5-Cl | H | 413.4 |
| 14 | CF$_3$ | OCHMe$_2$ | 2-F, 5-F | H | 459.1 |
| 15 | CF$_3$ | NHMe | 2-F, 5-F | H | 430.2 |
| 16 | CF$_3$ | H | 2-F, 3-Cl, 6-F | H | 435.2 |
| 17 | 4-CF$_3$-Ph | OH | 2-F, 5-F | H | 493 |
| 18 | 4-CF$_3$-Ph | H | 2-F, 5-F | H | 477.1 |
| 19 | CF$_3$ | H | 3-Cl, 4-F | H | 417.2 |
| 20 | CF$_3$ | H | 2-F, 4-Cl, 5-F | H | 435.0 |
| 21 | 4-F-Ph | H | 2-F, 5-F | H | 427 |
| 22 | CF$_3$ | H | 2-F, 3-F, 6-F | H | 419.2 |
| 23 | CF$_3$ | H | 2-F, 4-F, 6-F | H | 419.2 |
| 24 | H | H | 2-F, 5-F | H | 333 |
| 25 | 3-Pyridyl | H | 2-F, 5-F | H | 410.0 |
| 26 | Me | H | 2-F, 5-F | H | 347 |
| 27 | 3-F-Ph | H | 2-F, 5-F | H | 427 |
| 28 | Ph | H | 2-F, 5-F | H | 409 |
| 29 | NMe$_2$ | H | 2-F, 5-F | H | 376 |
| 30 | 4-morpholino | H | 2-F, 5-F | H | 418 |
| 31 | 4-OCF$_3$-Ph | H | 2-F, 5-F | H | 493 |
| 32 | Cyclopropyl | H | 2-F, 5-F | H | 373 |
| 33 | 4-NMe$_2$-Ph | H | 2-F, 5-F | H | 452 |
| 34 | 4-pyridyl | H | 2-F, 5-F | H | 410 |
| 35 | 4-SO$_2$Me-Ph | H | 2-F, 5-F | H | 487 |
| 36 | 3-Me-4-NO$_2$-imidazol-2-yl | H | 2-F, 5-F | H | 458 |
| 37 | 4-SO$_2$CF$_3$-Ph | H | 2-F, 5-F | H | 541 |
| 38 | Cyclopropyl | H | 2-F, 4-F, 5-F | H | 391 |
| 39 | 4-SO$_2$NH$_2$-Ph | H | 2-F, 5-F | H | 488 |
| 40 | NHCH$_2$Ph | H | 2-F, 5-F | H | 438.1 |
| 41 | 2-pyrazinyl | H | 2-F, 5-F | H | 411 |
| 42 | CF$_3$ | H | 2-F, 4-F, 5-F | Me | 433 |
| 43 | 4-Me-Ph | H | 2-F, 5-F | H | 423 |
| 44 | 3-Cl, 4-Cl-Ph | H | 2-F, 5-F | H | 477 |
| 45 | 4-SO$_2$Me-Ph | H | 2-F, 4-F, 5-F | H | 505 |
| 46 | CF$_3$ | H | 2-F, 5-F | Me | 415 |
| 47 | 4-Cl-Ph | H | 2-F, 5-F | H | 443 |
| 48 | 2-Cl-Ph | H | 2-F, 5-F | H | 443 |
| 49 | 2-F-Ph | H | 2-F, 5-F | H | 427 |
| 50 | 2-pyridyl | H | 2-F, 5-F | H | 410 |
| 51 | 4-CONH$_2$-Ph | CF$_3$ | 2-F, 5-F | H | 520.1 |
| 52 | 2-pyrazinyl | CF$_3$ | 2-F, 5-F | H | 479.0 |
| 53 | 4-NH$_2$-Ph | H | 2-F, 5-F | H | 424 |
| 54 | H | CF$_3$ | 2-F, 5-F | H | 401.1 |
| 55 | 4-SO$_2$Me-Ph | CF$_3$ | 2-F, 5-F | H | 555.1 |
| 56 | 4-SO$_2$Me-Ph | CF$_3$ | 2-F, 4-F, 5-F | H | 573.0 |
| 57 | 4-NHSO$_2$Me-Ph | H | 2-F, 5-F | H | 502 |

EXAMPLE OF A PHARMACEUTICAL FORMULATION

As a specific embodiment of an oral pharmaceutical composition, a 100 mg potency tablet is composed of 100 mg of any of the compounds of the present invention, 268 mg microcrystalline cellulose, 20 mg of croscarmellose sodium, and 4 mg of magnesium stearate. The active, microcrystalline cellulose, and croscarmellose are blended first. The mixture is then lubricated by magnesium stearate and pressed into tablets.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula I:

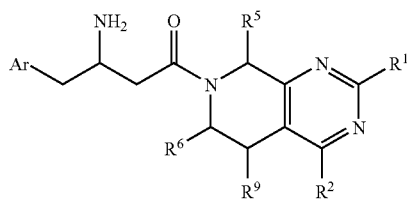

wherein:

Ar is phenyl which is unsubstituted or substituted with 1–5 of R$^3$, wherein R$^3$ is independently selected from the group consisting of:
(1) halogen,
(2) C$_{1-6}$alkyl, which is linear or branched and is unsubstituted or substituted with 1–5 halogens,
(3) OC$_{1-6}$alkyl, which is linear or branched and is unsubstituted or substituted with 1–5 halogens,
(4) CN, and
(5) OH;

R$^1$ and R$^2$ are independently selected from the group consisting of:
(1) hydrogen,
(2) CN,
(3) C$_{1-10}$alkyl, which is linear or branched and which is unsubstituted or substituted with:
(a) halogen, or
(b) phenyl, which is unsubstituted or substituted with 1–5 substituents independently selected from halogen, CN, OH, R$^4$, OR$^4$, NHSO$_2$R$^4$, N(C$_{1-6}$ alkyl)SO$_2$R$^4$, SO$_2$R$^4$, SO$_2$NR$^7$R$^8$, NR$^7$R$^8$, CONR$^7$R$^8$, CO$_2$H, and CO$_2$C$_{1-6}$alkyl, wherein the C$_{1-6}$alkyl is linear or branched,
(4) phenyl which is unsubstituted or substituted with 1–5 substituents independently selected from halogen, CN, OH, R$^4$, OR$^4$, NHSO$_2$R$^4$, N(C$_{1-6}$alkyl)SO$_2$R$^4$, SO$_2$R$^4$, SO$_2$NR$^7$R$^8$, NR$^7$R$^8$, CONR$^7$R$^8$, CO$_2$H, and CO$_2$C$_{1-6}$alkyl, wherein the C$_{1-6}$alkyl is linear or branched,
(5) a 5- or 6-membered heterocycle which may be saturated or unsaturated comprising 1–4 heteroatoms independently selected from N, S and O, the heterocycle being unsubstituted or substituted with 1–3 substituents independently selected from oxo, halogen, NO$_2$, CN, OH, R$^4$, OR$^4$, NHSO$_2$R$^4$, N(C$_{1-6}$alkyl)SO$_2$R$^4$, SO$_2$R$^4$, SO$_2$NR$^7$R$^8$, NR$^7$R$^8$, CONR$^7$R$^8$, CO$_2$H, and CO$_2$C$_{1-6}$alkyl, wherein the C$_{1-6}$alkyl is linear or branched,
(6) C$_{3-6}$cycloalkyl, which is optionally substituted with 1–5 substituents independently selected from halogen, OH, C$_{1-6}$alkyl, and OC$_{1-6}$alkyl, wherein the C$_{1-6}$alkyl and OC$_{1-6}$alkyl are linear or branched and optionally substituted with 1–5 halogens,
(7) OH,
(8) OR$^4$, and
(9) NR$^7$R$^8$;
R$^4$ is C$_{1-6}$alkyl, which is linear or branched and which is unsubstituted or substituted with 1–5 groups independently selected from halogen, CO$_2$H, and CO$_2$C$_{1-6}$alkyl, wherein the C$_{1-6}$alkyl is linear or branched;
R$^5$, R$^6$ and R$^9$ are independently selected from the group consisting of:
(1) hydrogen,
(2) C$_{1-10}$alkyl, which is linear or branched and which is unsubstituted or substituted with one or more substituents selected from:
(a) halogen,
(b) hydroxy,
(c) phenyl, which is unsubstituted or substituted with 1–5 substituents independently selected from halogen, OH, C$_{1-6}$alkyl, and OC$_{1-6}$alkyl, wherein the C$_{1-6}$alkyl is linear or branched and optionally substituted with 1–5 halogens,
(d) naphthyl, wherein the naphthyl is optionally substituted with 1–5 substituents independently selected from halogen, OH, C$_{1-6}$alkyl, and OC$_{1-6}$alkyl, wherein the C$_{1-6}$alkyl is linear or branched and optionally substituted with 1–5 halogens,
(e) CO$_2$H,
(f) CO$_2$C$_{1-6}$alkyl,
(g) CONR$^7$R$^8$,
(3) CN,
(4) phenyl which is unsubstituted or substituted with 1–5 substituents independently selected from C$_{1-6}$alkyl, OC$_{1-6}$alkyl, hydroxy and halogen, wherein the C$_{1-6}$alkyl is linear or branched and optionally substituted with 1–5 halogens,
(5) naphthyl which is unsubstituted or substituted with 1–5 substituents independently selected from C$_{1-6}$alkyl, OC$_{1-6}$alkyl, hydroxy and halogen, wherein the C$_{1-6}$alkyl is linear or branched and optionally substituted with 1–5 halogens,
(6) CO$_2$H,
(7) CO$_2$C$_{1-6}$alkyl,
(8) CONR$^7$R$^8$, and
(9) C$_{3-6}$cycloalkyl, which is unsubstituted or substituted with 1–5 substituents independently selected from halogen, OH, C$_{1-6}$alkyl, and OC$_{1-6}$alkyl, wherein the C$_{1-6}$alkyl is linear or branched and optionally substituted with 1–5 halogens;

R$^7$ and R$^8$ are independently selected from the group consisting of:
(1) hydrogen,
(2) phenyl, which is unsubstituted or substituted with substituents independently selected from halogen, OH, C$_{1-6}$alkyl, and OC$_{1-6}$alkyl, wherein the C$_{1-6}$alkyl is linear or branched and optionally substituted with 1–5 halogens,
(3) C$_{3-6}$cycloalkyl, which is unsubstituted or substituted with substituents independently selected from halogen, OH, C$_{1-6}$alkyl, and OC$_{1-6}$alkyl, wherein the C$_{1-6}$alkyl is linear or branched and optionally substituted with 1–5 halogens, and
(4) C$_{1-6}$alkyl, which is linear or branched and which is unsubstituted or substituted with:
(a) halogen, or
(b) phenyl, which is unsubstituted or substituted with 1–5 substituents independently selected from halogen, OH, C$_{1-6}$alkyl, and OC$_{1-6}$alkyl, wherein the C$_{1-6}$alkyl is linear or branched and optionally substituted with 1–5 halogens,
or wherein R$^7$ and R$^8$ together with the nitrogen atom to which they are attached form a heterocyclic ring selected from azetidine, pyrrolidine, piperidine, piperazine, and morpholine wherein said heterocyclic ring is unsubstituted or substituted with one to five substituents independently selected from halogen, hydroxy, C$_{1-6}$ alkyl, and C$_{1-6}$ alkoxy, wherein alkyl and alkoxy are unsubstituted or substituted with one to five halogens;
or a pharmaceutically acceptable salt thereof or an individual diastereomer thereof.

2. The compound of claim 1 of the formula Ia:

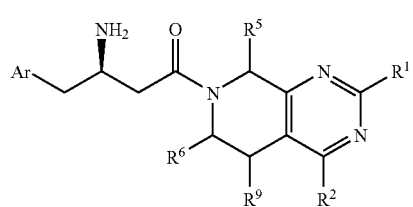

Ia wherein Ar, R$^1$, R$^2$, R$^5$, R$^6$ and R$^9$ are defined in claim 1;
or a pharmaceutically acceptable salt thereof or an individual diastereomer thereof.

3. The compound of claim 1 of the formula Ib:

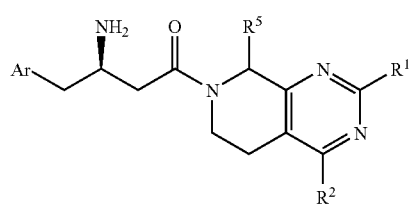

Ib wherein Ar, R$^1$, R$^2$ and R$^5$ are defined in claim 1;
or a pharmaceutically acceptable salt thereof or an individual diastereomer thereof.

4. The compound of claim 1 of the formula Ic:

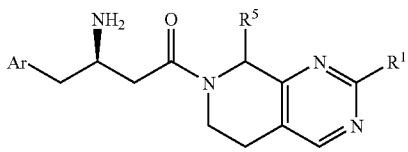

wherein Ar, $R^1$ and $R^5$ are defined in claim 1;
or a pharmaceutically acceptable salt thereof or an individual diastereomer thereof.

5. The compound of claim 1 of the formula Id:

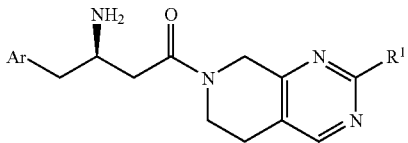

wherein Ar and $R^1$ are defined in claim 1;
or a pharmaceutically acceptable salt thereof or an individual diastereomer thereof.

6. The compound of claim 1 of the formula Ie:

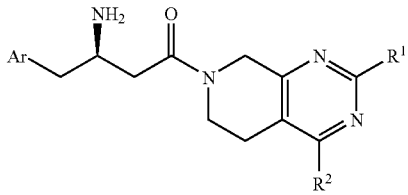

wherein Ar, $R^1$ and $R^2$ are defined in claim 1;
or a pharmaceutically acceptable salt thereof or an individual diastereomer thereof.

7. The compound of claim 1 wherein Ar is phenyl which is unsubstituted or substituted with 1–5 of $R^3$ which are independently selected from the group consisting of:
(1) fluoro,
(2) chloro,
(3) bromo,
(4) methyl,
(5) $CF_3$, and
(6) OH.

8. The compound of claim 1 wherein Ar is selected from the group consisting of:
(1) phenyl,
(2) 2-fluorophenyl,
(3) 3,4-difluorophenyl,
(4) 2,5-difluorophenyl, and
(5) 2,4,5-trifluorophenyl.

9. The compound of claim 1 wherein $R^1$ is selected from the group consisting of:
(1) hydrogen,
(2) $C_{1-6}$alkyl, which is linear or branched and which is unsubstituted or substituted with phenyl or 1–5 fluoro,
(3) phenyl which is unsubstituted or substituted with 1–5 substituents independently selected from halogen, CN, OH, $R^4$, $OR^4$, $NHSO_2R^4$, $N(C_{1-6}alkyl)SO_2R^4$, $SO_2R^4$, $SO_2NR^7R^8$, $NR^7R^8$, $CONR^7R^8$, $CO_2H$, and $CO_2C_{1-6}$alkyl, wherein the $C_{1-6}$alkyl is linear or branched,
(4) a 5- or 6-membered heterocycle which may be saturated or unsaturated comprising 1–4 heteroatoms independently selected from N, S and O, the heterocycle being unsubstituted or substituted with 1–3 substituents independently selected from oxo, halogen, $NO_2$, CN, OH, $R^4$, $OR^4$, $NHSO_2R^4$, $N(C_{1-6}alkyl)SO_2R^4$, $SO_2R^4$, $SO_2NR^7R^8$, $NR^7R^8$, $CONR^7R^8$, $CO_2H$, and $CO_2C_{1-6}$alkyl, wherein the $C_{1-6}$alkyl is linear or branched,
(5) $C_{3-6}$cycloalkyl, and
(6) $NR^7R^8$.

10. The compound of claim 1 wherein $R^1$ is selected from the group consisting of:
(1) hydrogen,
(2) $CF_3$,
(3) phenyl which is unsubstituted or substituted with 1–5 substituents independently selected from halogen, methyl, $CF_3$, $OCF_3$, $NHSO_2Me$, $NHSO_2CF_3$, $SO_2Me$, $SO_2CF_3$, $SO_2NH_2$, $NH_2$, $NHMe$, $NMe_2$, and $CONH_2$,
(4) pyridine, pyrazine, and imidazole which is unsubstituted or substituted with 1–5 substituents independently selected from $CF_3$, Me, and $NO_2$,
(5) cyclopropyl,
(6) morpholine,
(7) $NH_2$,
(8) NHMe,
(9) $NMe_2$, and
(10) $NHCH_2Ph$.

11. The compound of claim 1 wherein $R^1$ is selected from the group consisting of:
(1) hydrogen,
(2) $CF_3$,
(3) phenyl which is unsubstituted or substituted with 1–5 substituents independently selected from halogen, methyl, $CF_3$, $OCF_3$, $NHSO_2Me$, $SO_2Me$, $SO_2CF_3$, $SO_2NH_2$, and $CONH_2$,
(4) pyridine, pyrazine, or imidazole which is unsubstituted or substituted with 1–5 substituents independently selected from $CF_3$, Me, and $NO_2$, and
(5) cyclopropyl.

12. The compound of claim 1 wherein $R^1$ is hydrogen or $CF_3$.

13. The compound of claim 1 wherein $R^2$ is selected from the group consisting of:
(1) hydrogen,
(2) $C_{1-6}$alkyl, which is linear or branched and which is unsubstituted or substituted with 1–5 fluoro,
(3) OH,
(4) $OR^4$, and
(5) $NR^7R^8$.

14. The compound of claim 1 wherein $R^2$ is selected from the group consisting of:
(1) hydrogen,
(2) OH,
(3) methoxy,
(4) isopropoxy,
(5) $CF_3$,
(6) $NH_2$, and
(7) NHMe.

15. The compound of claim 1 wherein $R^2$ is hydrogen.

16. The compound of claim 1 wherein $R^5$, $R^6$ and $R^9$ are independently selected from the group consisting of:
(1) hydrogen, and
(2) $C_{1-10}$alkyl, which is linear or branched and which is unsubstituted or substituted with one or more substituents selected from:
(a) halogen, and
(b) phenyl, wherein the phenyl is optionally substituted with 1–5 substituents independently selected from halogen, OH, $C_{1-6}$alkyl, and $OC_{1-6}$alkyl, wherein the $C_{1-6}$alkyl and $OC_{1-6}$alkyl are linear or branched and optionally substituted with 1–5 halogens.

17. The compound of claim 1 wherein $R^5$, $R^6$ and $R^9$ are independently selected from the group consisting of:
(1) hydrogen,
(2) $CH_3$, and
(3) $CH_2$-phenyl.

18. The compound of claim 1 wherein $R^5$ is H or $CH_3$ and $R^6$ and $R^9$ are hydrogen.

19. A compound which is selected from the group consisting of:

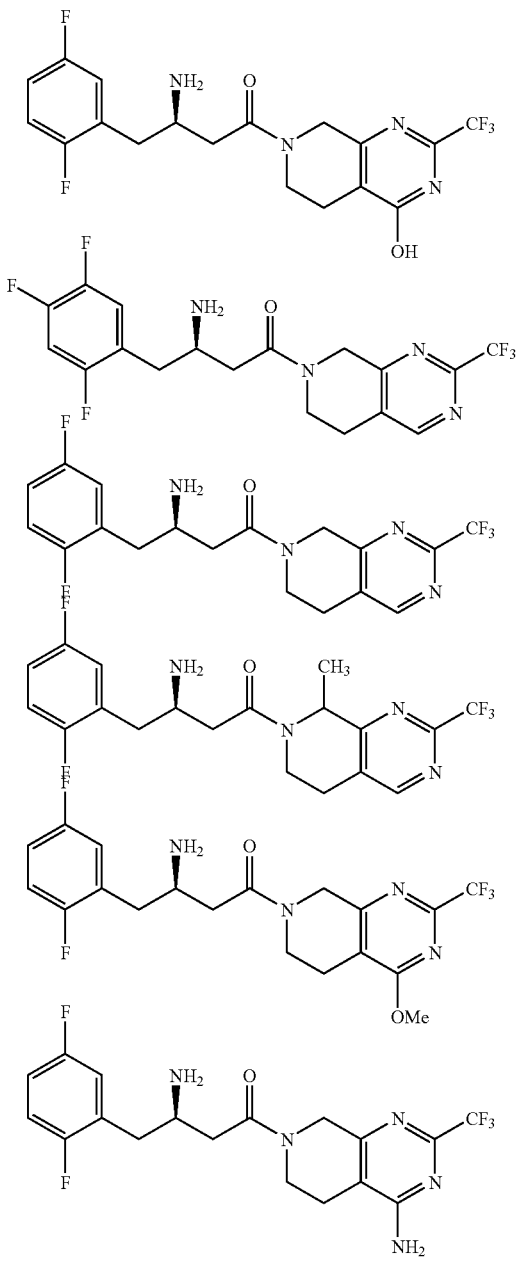

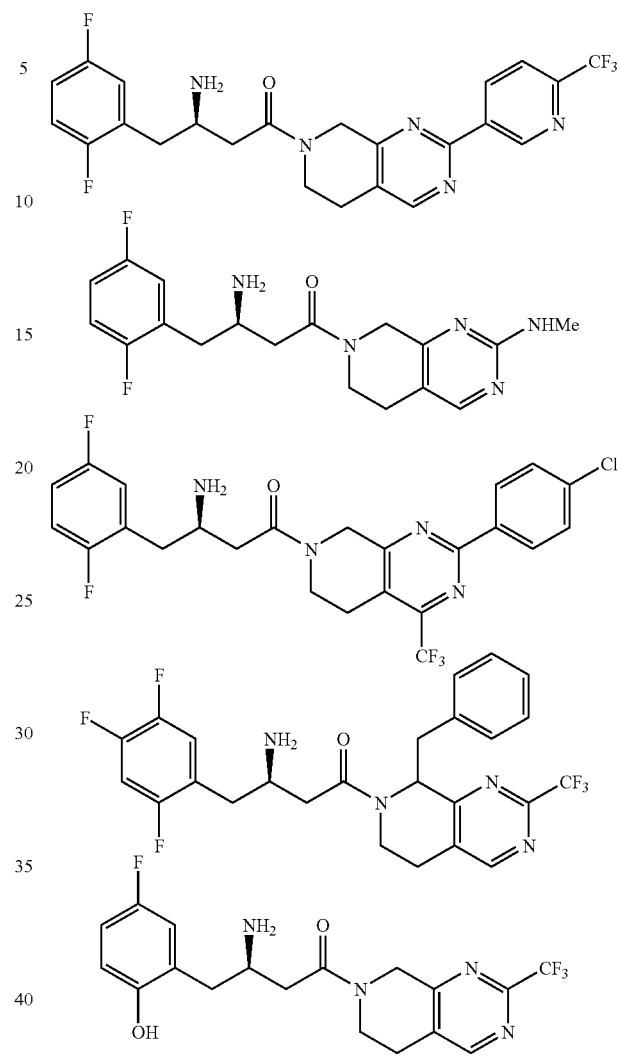

or a pharmaceutically acceptable salt thereof.

20. A pharmaceutical composition which comprises an inert carrier and a compound of claim 1.

21. A method of treating Type II diabetes comprising administering to a mammalian patient in need of such treatment a therapeutically effective amount of a compound of claim 1.

* * * * *